United States Patent [19]

Funk

[11] Patent Number: 4,972,155
[45] Date of Patent: Nov. 20, 1990

[54] WEIGHT RESPONSIVE MOISTURE TESTER
[75] Inventor: Robert C. Funk, Auburn, Ill.
[73] Assignee: Dickey-John Corporation, Auburn, Ill.
[21] Appl. No.: 277,322
[22] Filed: Nov. 29, 1988
[51] Int. Cl.$^5$ .............................................. G01R 27/26
[52] U.S. Cl. ...................................... 324/669; 324/689
[58] Field of Search .................. 324/61 R, 61 P, 679, 324/669, 670, 685, 689; 340/613, 617, 616; 222/39, 40, 55, 56, 77; 177/45–48, 225

[56] References Cited

U.S. PATENT DOCUMENTS

| | | | |
|---|---|---|---|
| 3,691,457 | 9/1972 | Kriellaars | 324/669 |
| 3,794,911 | 2/1974 | Fathauer | 324/61 R |
| 4,080,563 | 3/1978 | Marsh et al. | 324/61 R |
| 4,121,151 | 10/1978 | Funk et al. | 324/61 R |
| 4,193,116 | 3/1980 | Funk | 324/61 R |
| 4,382,527 | 5/1983 | Lerner | 222/56 |
| 4,578,874 | 4/1986 | Juengel | 340/652 |
| 4,584,655 | 4/1986 | Funk et al. | 324/61 R |

FOREIGN PATENT DOCUMENTS

| | | | |
|---|---|---|---|
| 0217495 | 4/1987 | European Pat. Off. | 324/61 R |
| 1416640 | 12/1975 | United Kingdom | 324/61 R |
| 2180937 | 4/1987 | United Kingdom | 324/61 R |

Primary Examiner—Reinhard J. Eisenzopf
Assistant Examiner—Maura K. Regan
Attorney, Agent, or Firm—Richard Bushnell

[57] ABSTRACT

A test apparatus for determining a given property, by weight, such as moisture content, of a material such as a grain or the like, comprises a chamber for receiving a sample of material to be tested, having an open top portion through which the material may be introduced therein for testing. An electrical circuit is operatively coupled with the chamber for producing an electrical measurement signal corresponding to the property to be determined and an indicator provides an observable indication of the given property of material in accordance with the corresponding electrical measurement signals. A measurement initiating control in responsive to the accumulation of a predetermined measurement weight of material in the chamber for initiating the operation of the circuit. A further warning control is responsive to the weight of material in the chamber reaching a second, predetermined warning weight slightly less than the predetermined measurement weight for producing a warning signal. The indicator is responsive to the warning signal for producing a warning indication for alerting the operator to introduce material into the chamber more slowly to thereby reduce the inertia of material entering the chamber as the measurement weight is approached, to facilitate accuracy of the determination of the given property of material, by weight.

13 Claims, 5 Drawing Sheets

WEIGHT RESPONSIVE MOISTURE TESTER

BACKGROUND OF THE INVENTION

A portion of the disclosure of this patent document contains material which is subject to copyright protection. The copyright owner has no objection to facsimile reproduction by anyone of the patent document or the patent disclosure, as it appears in the Patent and Trademark Office patent file or records, but otherwise reserves all copyright rights whatsoever.

The present invention is directed to the field of test instruments and test apparatus for determining properties of material. More particularly, the present invention is concerned with a novel moisture tester for determining the moisture content of any of a plurality of different grain or grain-like materials.

Since grain moisture is defined as a percentage by weight of moisture, it is necessary to use a sample of known weight in order to obtain an accurate moisture reading. Some prior art systems have accomplished this by separately weighing out a test sample prior to introduction thereof into a test instrument. However, this procedure is somewhat cumbersome and time consuming.

One particularly useful and successful weight-responsive type of moisture tester is shown in U.S. Pat. No. 3,794,911, assigned to the assignee of this application. This weight-responsive moisture tester is arranged to automatically perform the moisture measurement when the weight of a sample introduced into the test apparatus reaches a given, predetermined weight, thereby eliminating a need to separately weigh out the sample prior to testing. Moreover, this novel patented device also utilizes a temperature compensation arrangement to compensate the moisture reading for variations from a standard or reference temperature.

While the foregoing patented device has enjoyed wide-spread acceptance, there is room for yet further improvement. For example, some compensation for the inertia effect of the pouring of material into the apparatus is desirable. The foregoing patented apparatus provided such compensation by utilizing a small built-in time delay to prevent the actual measurement from taking place for a very short period following the sample reaching the desired weight, to attempt to compensate for inertia and to allow the apparatus to stabilize.

We propose to improve upon the foregoing system by additionally providing a built-in warning system, wherein the operator is warned, just prior to reaching the weight at which the measurement is made, to slow the rate of pouring of material into the apparatus somewhat to avoid excessive inertia effects. We have also developed a novel inertia compensation method for further compensating for differences in inertia caused by differences in pouring rate while introducing material into the test apparatus.

We have also found that it is important to confine the forces exerted upon the test apparatus by the material substantially to the vertical direction to assure proper response for weight measurement purposes. Accordingly, we have proposed using novel torsion resisting means for substantially avoiding the pouring of material from exerting a torsioning or twisting motion upon the apparatus.

In addition to the foregoing, the apparatus of the invention also provides improved temperature compensation, which will accurately predict the actual temperature of grain in the apparatus, without regard for the speed with which the grain is introduced into the test apparatus. Moreover, our arrangement determines when the prediction has converged sufficiently to assure a stable and accurate temperature reading and corresponding compensation.

The test apparatus of the invention further includes memory for retaining calibration and other data for the measurement of as many as 12 different materials. More importantly, we have provided a novel low-cost and easy to use infrared programming link built into the test apparatus so that the apparatus may be normalized, configured for a particular set of features and supplied with calibrations as the last step of manufacture. Alternately, the calibration may be done by a dealer, if desired, without making a physical intrusion or alteration of the apparatus and without making electrical connection to the electronic components thereof.

OBJECTS AND SUMMARY OF THE INVENTION

It is therefore an object of this invention to provide a novel and improved test apparatus in accordance with the foregoing discussion.

Briefly, and in accordance with the foregoing, a test apparatus for determining a given property, by weight, such as moisture content, of a material such as a grain or the like, comprises wall means forming a chamber for receiving a sample of material to be tested, said chamber having an open top portion through which the material may be introduced therein for testing; electrical circuit means operatively coupled with said chamber for producing an electrical measurement signal corresponding to the said given property to be determined; indicator means for providing an observable indication of the said property of material in accordance with the corresponding electrical measurement signals; initiating means responsive to the accumulation of a predetermined measurement weight of material in said chamber for initiating the operation of said circuit means; said indicating means further including warning means responsive to the weight of material in said chamber reaching a second, predetermined warning weight slightly less than said predetermined measurement weight for producing a warning signal; said indicator means being response to said warning signal for producing a warning indication for alerting the operator to introduce material into the chamber more slowly to thereby reduce the inertia of material entering the chamber as the measurement weight is approached, to facilitate accuracy of the determination of the said given property of material, by weight.

In accordance with another aspect of the invention, a test apparatus for determining a given property, by weight, such as moisture content, of a material such as a grain or the like, comprises a test chamber for receiving a sample of material to be tested, said chamber having an open top portion through which the material may be introduced therein for testing; and electrical circuit means operatively coupled with said chamber for producing an electrical measurement signal corresponding to the said given property to be determined; wherein said circuit means includes memory means for containing predetermined data and information for determining the said given property of a plurality of different materials in accordance with said measurement signal, and further including infrared programming link means for permitting access to said memory means for varying the data and information contained therein.

BRIEF DESCRIPTION OF THE DRAWINGS

The features of the present invention which are believed to be novel are set forth with particularity in the appended claims. The organization and manner of operation of the invention, together with further objects and advantages thereof, may best be understood by reference to the following description taken in connection with the accompanying drawings in which like reference numerals identify like elements, and in which:

DETAILED DESCRIPTION OF THE ILLUSTRATED EMBODIMENT

Figure 1:
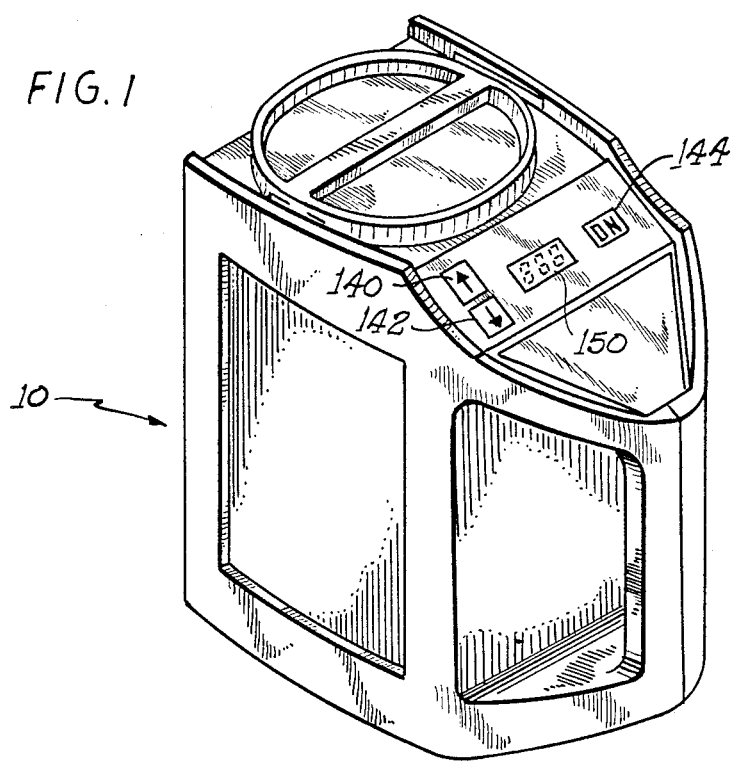
FIG. 1 is a perspective view of a moisture tester in accordance with the present invention.
Figure 3:
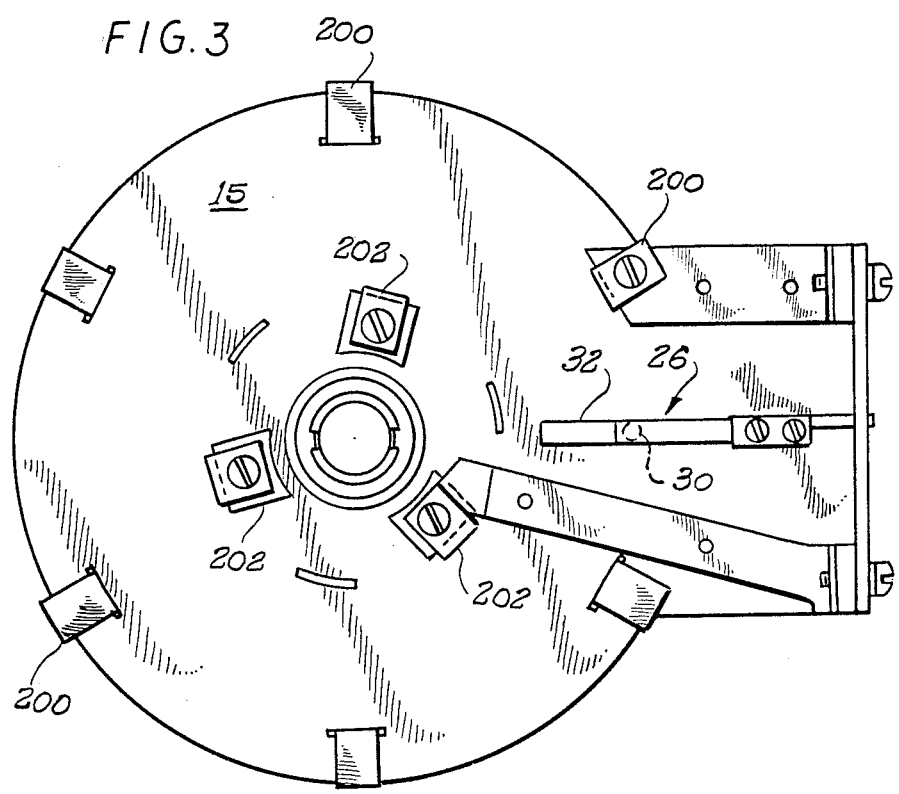
FIG. 3 is a view taken generally along the line 3—3 of FIG. 2.
Figure 2:
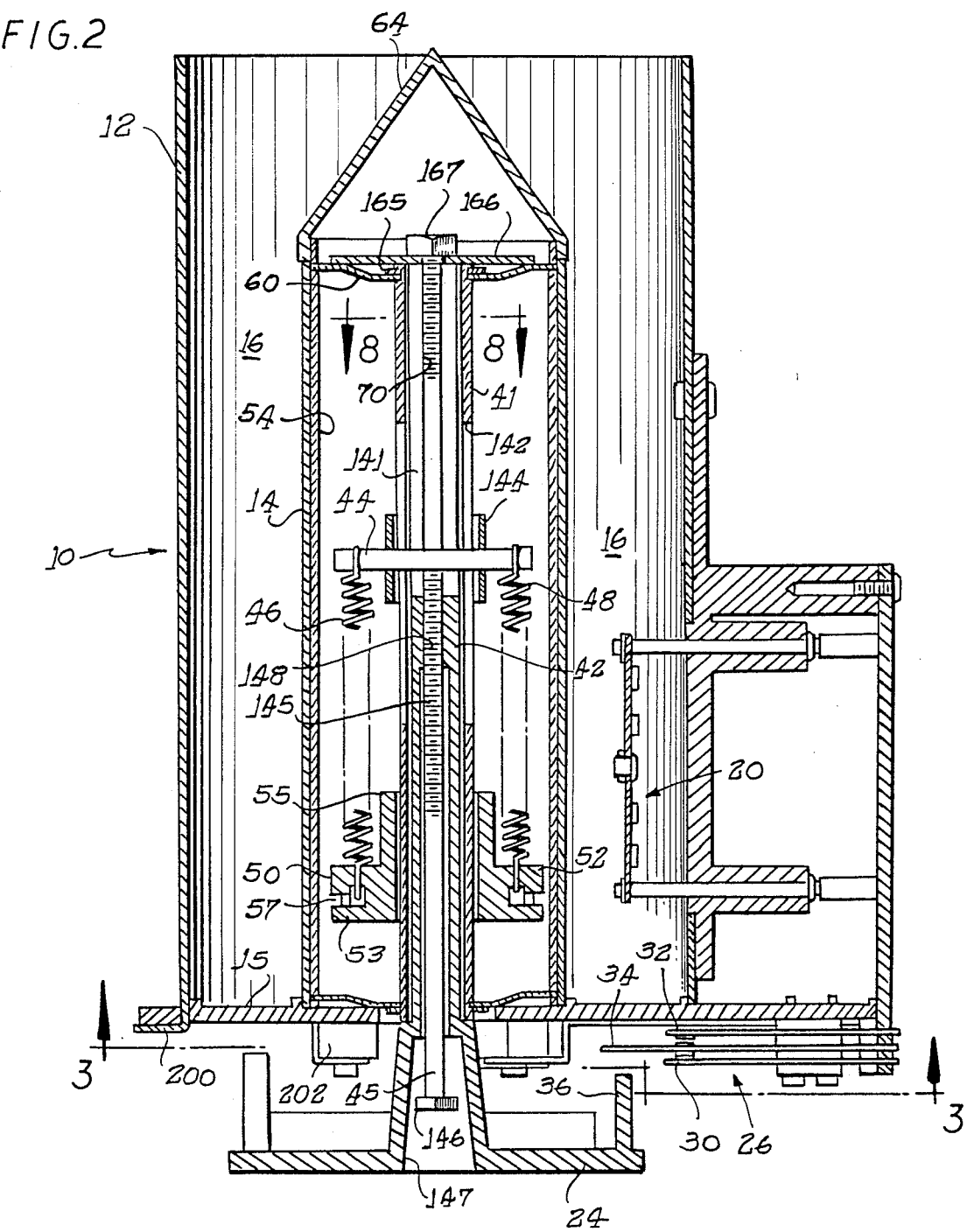
FIG. 2 is an enlarged sectional side elevation of the tester of FIG. 1.
Figure 8:
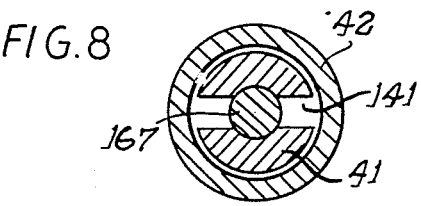
FIG. 8 is a sectional view taken generally along the line 8—8 of FIG. 2.

Referring now to the drawings, and initially to FIGS. 1-3, a test apparatus in accordance with the invention is designated generally by the reference numeral 10. In accordance with the preferred form of the invention illustrated and described herein, the test apparatus 10 comprises a moisture tester for determining the moisture content of a material such as a grain or the like by weight. However, it will be understood that the principles of the invention may find application in the determination of other properties of grain, or of other materials, without departing from the invention.

The moisture tester 10 of the illustrated embodiment comprises a pair of walls or wall means 12, 14 which define or form therebetween a chamber 16 for receiving a quantity or sample of the material to be tested. This chamber 16 has an open top 18 through which the material may be introduced therein for testing. Cooperating electrical circuit means are somewhat diagrammatically illustrated at 20, further details thereof being shown in circuit schematic form in FIGS. 5 and 6. These electrical circuit means 20 are operatively coupled with the chamber 16 for producing an electrical measurement signal corresponding to the property of material to be determined.

In the illustrated embodiment, the wall means 12, 14 forming chamber 16 comprise generally concentrically formed cylindrical inner and outer walls which define a generally annular open-topped chamber therebetween, as best viewed in FIG. 2. The outer and inner walls 12, 14 are also arranged electrically with circuit 20 to form plates of a capacitor. Bottom wall 15 is generally circular in form and receives and supports respective outer and inner wall members 12, 14 so as to provide a bottom closure for the chamber 16 defined therebetween.

The circuit 20 is operatively electrically coupled with the capacitor thus formed for measuring the impedance properties thereof both with material present in chamber 16 and with material absent from chamber 16. By comparing these impedance measurements, the contribution of the material to the net impedance measured across the chamber may be determined. Once this net impedance contribution and the weight of the material are known, various properties, such as the moisture content thereof, can be calculated. In accordance with the preferred form of the invention herein illustrated, the circuit means 20 also includes appropriate microprocessor-type circuits for performing all of the necessary measurements and calculations, and moreover, for driving a suitable display (to be described later hereinbelow) for giving a direct reading of the measured moisture content to an operator.

In accordance with an important feature of the invention, initiating means are provided which are responsive to the accumulation of a predetermined "measurement" weight of material in the chamber for initiating the operation of the circuit means for performing the necessary measurement upon the material to determine the moisture content thereof. In the illustrated embodiment, the initiating means include resilient means 46, 48 which support or suspend the chamber 16 relative to a fixed base member or base portion designated generally by reference numeral 24, and a circuit element 26. The resilient mounting of the chamber relative to the base 24 is so arranged that the aforementioned predetermined measurement weight of material will cause sufficient movement therebetween to change the condition of the circuit element 26 which is coupled to detect relative motion between the chamber 16 and base 24. In the illustrated embodiment, the circuit element 26 takes the form of a switch having a pair of contacts 30 and 32 and a contactor 34 which is movable therebetween. Preferably, one of the contacts 30, 32 is a normally open contact and the other is a normally closed contact, such that movement of the contactor 34 therebetween will change the operative electrical states thereof in a manner detectable by the circuit means 20.

In the illustrated embodiment, it will be seen that the contactor 34 is urged from a rest position in electrically conductive contact with the contact member 30 by a projecting actuator element 36. This actuator element 36 projects upwardly from the base 24 a predetermined distance, such that during relative downward movement of the chamber 16, the actuator 36 will press the movable contactor 34 first out of contact with normally open contact 30 and finally into electrically conductive contact with normally closed contact 32. Preferably this latter contact with contact 32 occurs upon the weight of the material in the chamber 16 reaching the predetermined measurement weight. In accordance with the preferred embodiment illustrated and described herein this predetermined measurement weight is substantially on the order of 200 grams. However, it will be appreciated that different measurement weights may be selected and appropriate adjustment made upon the elements of the invention for accommodating the same, without departing from the invention.

In the illustrated embodiment, the initiating means, designated generally by reference numeral 40 in FIG. 1 includes, in addition to the switch 26, actuator 36 and resilient means 46, 48, further suspension elements or means for supporting the resilient means 46, 48. In the illustrated embodiment these supporting means include respective inner and outer elongate, hollow, tube-like supporting members or frame members 41, 42. Preferably, inner supporting member or tube 41 is integrally formed with base 24 and extends upwardly therefrom. Outer supporting member or tube 42 is generally coaxial with and surroundingly engages inner tube 41 and preferably rests on a shoulder 43 formed where the inner tube 41 meets the base 24. Preferably, these tube-like support or frame members 41, 42 are located coaxially within the inner wall member 14.

Additional spring mounting means comprise a rod-like member or hanger bar 44 which extends transversely through the respective tube members 41, 42. Preferably respective elongate slots 141, 142 are formed at diammetrically opposed sides of the respective tubes 41, 42 for receiving the rod 44 therethrough. These elongate slots also permit upward and downward adjustment of the rod 44 for adjusting the tensioning on a pair of springs 46, 48 which comprise the resilient means, as will be more fully described hereinbelow.

The hanger bar 44 is further supported proximate its center by an elongate support rod 45 which extends coaxially through the inner tubular support member 41 from the base 24. This rod-like support member 45 is preferably externally threaded as indicated at 145 and has a driver head 146 which is housed within a recess 147 formed within the base 24. The thread 145 engages a complementary internal thread 148 formed on the interior of tubular support 41. Accordingly, rod 45 may be extended and retracted relative to tube 41 for correspondingly raising and lowering the level of the hanger rod 44. Preferably, hanger rod 44 is further supported by a cylindrical skirt 144 which surroundingly engages outer tube 42, and through which rod 44 also passes. This additional support also helps to avoid tilting or wobbling of the rod 44 relative to the support or adjusting rod 45, and to maintain respective springs 46 and 48 substantially equally tensioned at all times. Preferably, these springs comprises substantially identical helical tension springs.

The springs in turn resiliently support chamber 16 from the support rod 45, to thus resiliently support the chamber relative to the base 24. The opposite ends of the respective springs 46, 48 are coupled with a pair of mounting brackets or ears 50, 52 formed on a flared skirt portion 53 of a tubular sleeve member 55 which surroundingly engages the tubular support or frame member 42. This sleeve member 55 is held in place by a plurality of tabs 57 which are struck out from an inner wall member or portion 54 which is preferably integrally attached to an inner surface of the inner wall member 14. This inner wall member or portion 54 in addition to providing a place for mounting the member 55 and its spring-mounting ears or flanges 50, 52 also provides cut out areas 61, 63 for receiving a pair of spiral flexures 60, 62 which will be discussed further hereinbelow, and with reference to FIG. 9. A cone-like cap member 64 also mounts to and extends upwardly from the inner wall member 14 for directing material into annular chamber 16 as material is introduced through its open top 18.

In operation, the spring means 46, 48 thereby provide resilient means which bias the entire chamber in a generally upward direction relative to the base 24. The support rod 55 may thus be used for fine tuning or adjusting the amount of pretensioning or bias provided by the springs 46, 48. This arrangement also serves to adjust the relative distance, when the chamber 16 is empty, between the contactor 34 and actuator 36. Accordingly, the member 45 is preferably adjusted so as to assure the desired movement of contactor 34 between the contacts 30 and 32 as material is introduced to the chamber, and to assure that the contactor 34 reaches the contact 30 when this material reaches the predetermined measurement weight.

In accordance with the embodiment of the invention illustrated herein, the resilient means also includes torsion means in the form of the above-mentioned spiral flexure elements 60 and 62. These elements tend to resist rotational or torsional motion of the chamber 46 relative to the base. This advantageously aids in assuring that the introduction of material into the chamber results in primarily an exertion of downward force upon the base and consequent actuation of the switching element 26.

Figure 9:
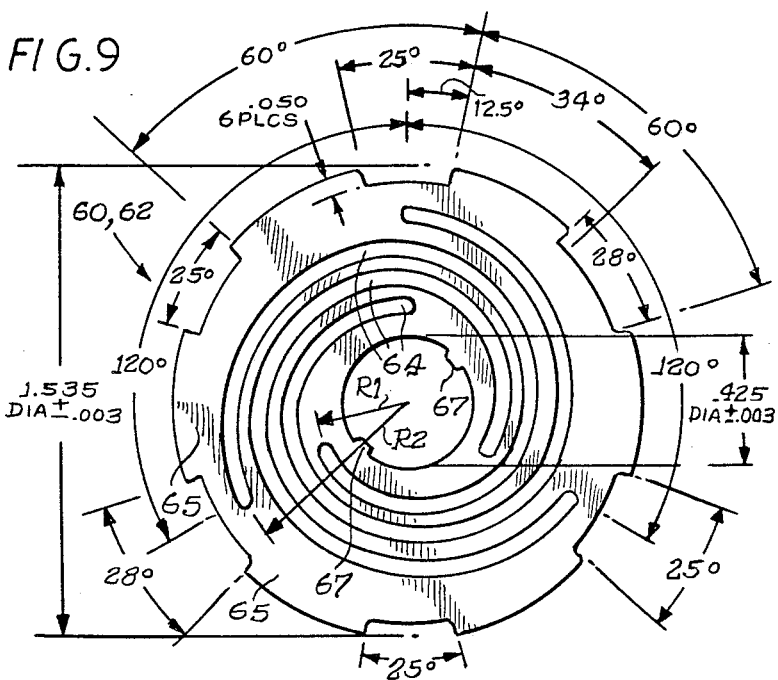
FIG. 9 is a plan view of a spiral flexure member of the tester shown in FIGS. 1-4.

Referring also to FIG. 9, it will be seen that the spiral flexures comprise generally flat, disc-like bodies which have a plurality of generally annular through slots or openings 64 formed therein. As best viewed in FIG. 9, these slots are preferably formed in accordance with a formula: $Ri = R1 + (R2-R1) A/360$, wherein $Ri$ = radius of a slot at a given point i, A = the angle from the minimum radius of the slot at R1 to the point Ri, R1 equals the minimum radius, R2 equals the maximum radius. It should be recognized, however, that other forms of anti-torsioning means may be utilized without departing from the invention.

Figure 4:
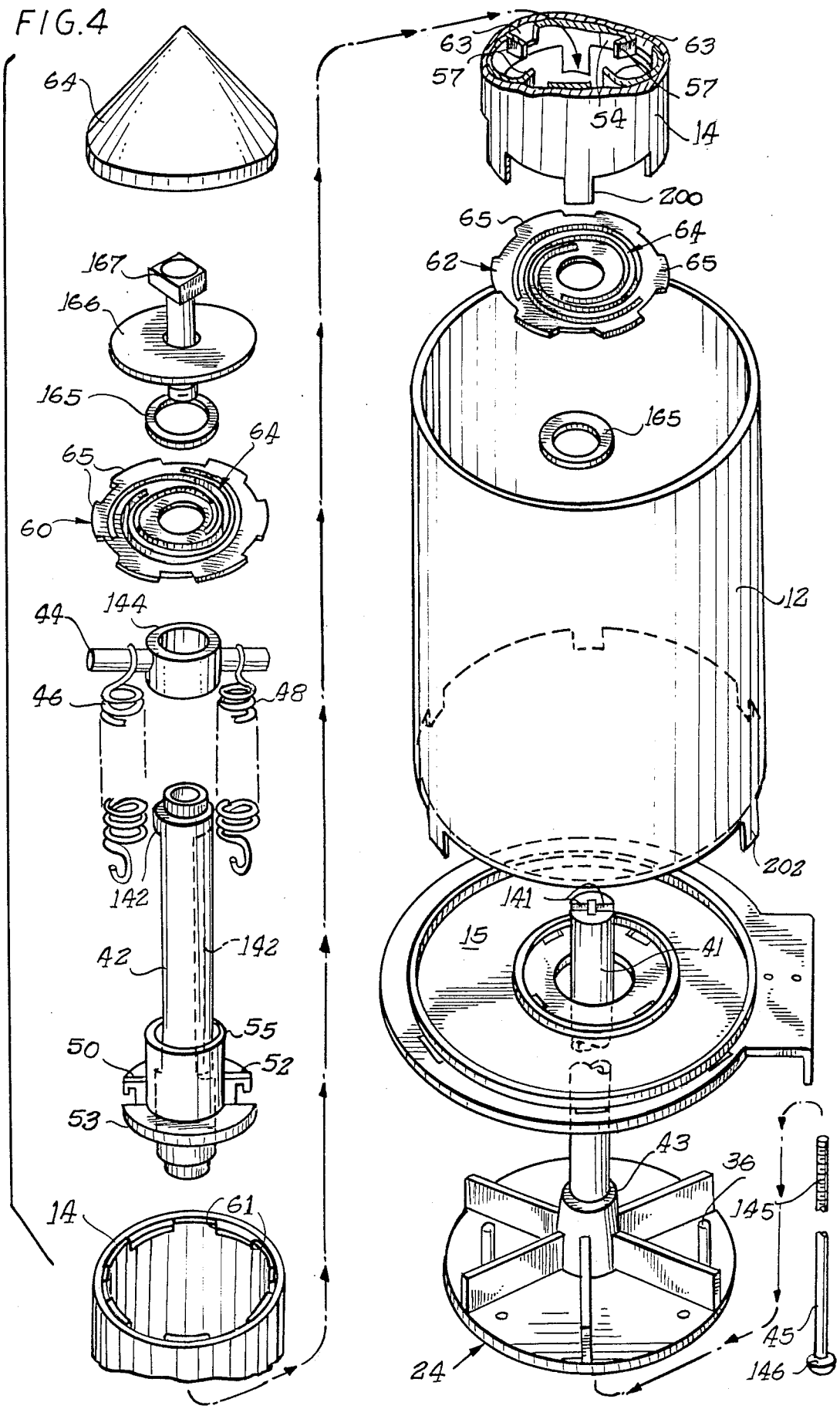
FIG. 4 is an exploded perspective view illustrating further details of the moisture tester of the invention.

Referring also to FIGS. 2 and 4, the respective spiral flexure members 60, 62 are attached at their outer margins by means of a plurality of projecting tabs 65 which interfit with and engage corresponding cut outs or notches 61, 63 in inner Wall member 54, generally adjacent the top and bottom edges of the inner wall member 14. Cooperatively, inner margins of the spiral flexure members are provided with inwardly extending locating tabs 67 for mating with similar locating cut outs (not shown) at upper and lower ends of the support or frame tubes 41, 42.

Moreover, the tube 42 is somewhat shorter than tube 41 to provide respective shoulders with an extending terminal end portion of inner support tube 41 to either end thereof. This shoulder and projecting portion of tube 41 provide means for mounting the spiral flexures as well as respective support washer members 165 therefor to either end of the tubular support 42. The extending ends of tubular support 41 are then struck over, to firmly engage the flexures 65 and their corresponding support washers 165 against respective ends of the support tube 42, as best viewed in the assembled view of FIG. 2. An additional enlarged uppermost washer 166 is interposed over the spiral flexure 65 and its washer 165 at the top end of the assembly to form a protective cover therefor, and also to provide a means for receiving an assembly bolt 167 which extends through the respective washers 165, 166 and spiral flexure 65 to engage a complementary internal thread 70 in the inner support tube 41, to hold the assembly together in the assembled relation indicated in FIG. 2.

Accordingly, the spiral flexures resist twisting of the structure so as to maintain the central axes of the respective springs 46 and 48 essentially parallel with each other and with the central axis of support post or member 42. This substantial elimination of torsional forces as between the chamber and the base thus substantially confines forces exerted upon the chamber during introduction of material therein to a direction for acting against the biasing force of the springs 46 and 48. This direction in the illustrated embodiment corresponds to a direct vertical downward force to thus cause only a relatively straight line motion as between actuator 36 and contactor 34, corresponding to the motion between the chamber 16 and base 24 caused by the introduction of material into the chamber.

In accordance with a further and related important feature of the invention, the circuit means 20 is adapted for response to the switch or circuit element 26 reaching a state in which the contactor 34 is initially engaged by actuator 36, such that it is in electrical contact with neither of the contacts 30 and 32. This condition will take place when a predetermined weight of material is in the chamber, during the pouring of material through the open top 18 thereof, just slightly prior to the weight of material reaching the predetermined measurement weight. We have referred to this second predetermined weight herein as a predetermined "warning weight". Hence, when the weight of material in the chamber is such as to just initially move contactor 34 out of contact with normally closed contact 30, the circuit means will produce a warning signal, and indicator means on the display panel (to be more fully described hereinbelow) will warn the operator to slow the rate of pouring or introduction of material into the chamber 18. This slowing of the rate of pouring as the material in the chamber approaches the measurement weight helps to reduce inertia effects of the pouring activity upon the springs, and related apparatus described hereinabove, in order to facilitate a greater accuracy and repeatability in the manner in which the switch or other circuit element reaches the state at which the measurement signal is given to initiate the measurement process by the circuit 20.

Figure 5:
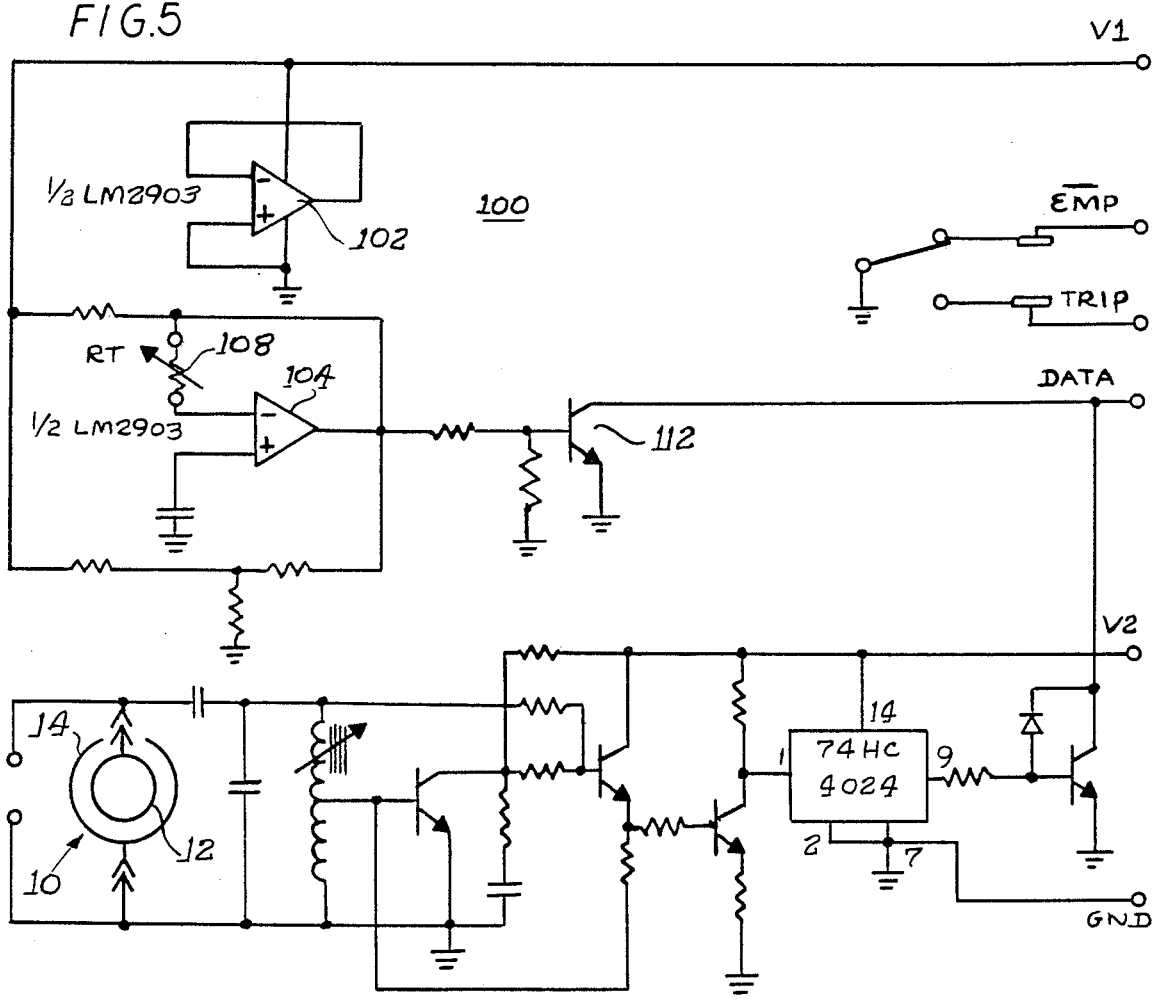
FIG. 5 is a circuit schematic diagram illustrating a portion of an electrical circuit of the moisture tester of the invention.
Figure 6:
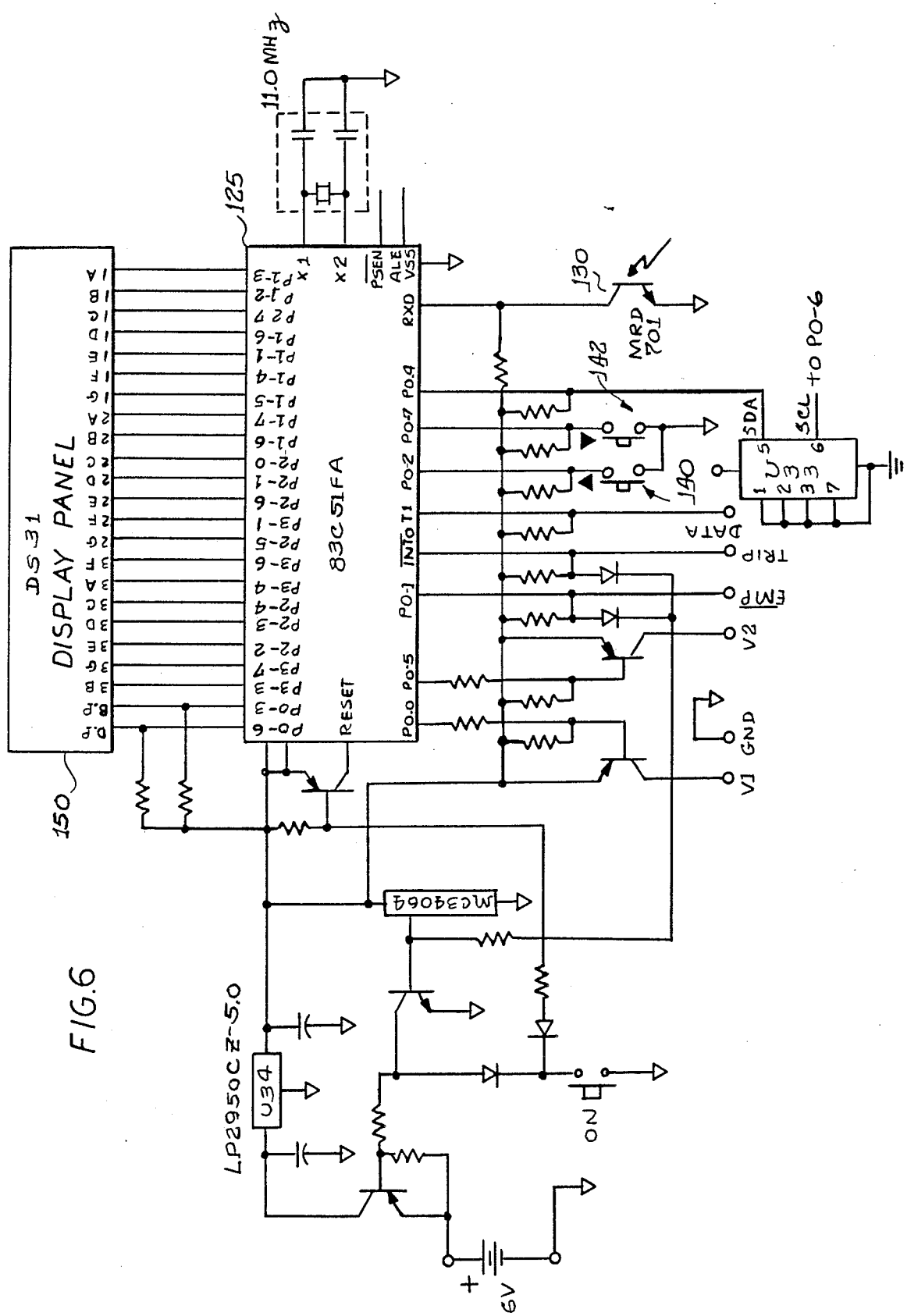
FIG. 6 is further circuit schematic diagram illustrating a further portion of the circuit in accordance with the invention.

Reference is next invited to FIGS. 5 and 6 wherein the circuit means 20 are illustrated in further detail in circuit schematic form. In accordance with the preferred feature of the embodiment illustrated herein, the circuit means 20 include temperature compensation circuit means illustrated in FIG. 5 which produce a temperature compensation signal for varying or adjusting the value of the readout produced in response to the measurement signal in accordance with the variation in the measured temperature of a given sample of material in the chamber 16 from a predetermined reference temperature.

This circuit, designated generally by reference numeral 100, includes a pair of operational amplifiers (op amps) 102, 104. These two op amps preferably comprise the two elements of a single integrated circuit dual op-amp component of the type generally designated LM2903. Reference voltage V1 is applied through a resistor to the non-inverting input of op amp 104 and also to a temperature sensitive element in the form of a thermistor (RT) 108. This in turn supplies a temperature dependent voltage at the inverting input of the op amp 104. The signals from the op amp 104 are buffered by a transistor 112 and fed out on the DATA line to the circuit of FIG. 6, whose major element is a microprocessor or microcomputer component 125 of the type designated either 83C51FA or 87C51FA available from Intel.

A test cell circuit 120 is electrically coupled in the manner indicated with the respective inner and outer walls 14, 12 of the test cell of FIG. 2 and provides outputs to the like-numbered inputs V2 and GND of the circuit of FIG. 6, to the microprocessor illustrated therein. These outputs carry the electrical signal corresponding to the property to be measured, which in the illustrated embodiment is the moisture of a sample of material in the test chamber. Switch 26 is also shown in FIG. 5, indicating its connections with the circuit of FIG. 6.

In accordance with a further feature of the illustrated embodiment, the circuit of FIG. 6 includes memory means, which preferably comprises on-board memory of the microprocessor of microcomputer 125. This memory means contains predetermined data and information for determining the desired property (e.g., moisture content by weight) of a plurality of different materials in accordance with the measurement signal obtained from the test chamber.

In accordance with a further feature of the illustrated embodiment, a novel infrared programming link means is provided for permitting access to the microprocessor and in particular to the on board memory means for varying the data and information contained therein. This in turn permits field testing, calibration, or the like without physically disturbing the circuit and without the need for establishing any electrical connection therewith. In the illustrated embodiment, the infrared link comprises a phototransistor element 130 which is coupled with the microprocessor 125 as illustrated in FIG. 6.

Figure 7:
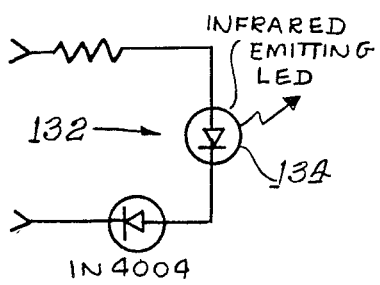
FIG. 7 is a further circuit schematic view illustrating the use of an infrared programming link feature of the moisture tester of the invention.

Referring briefly to FIG. 7, a relatively simple apparatus may be utilized to convert digital information to infrared pulses detectable by the phototransistor 130. This circuit is designated in FIG. 7 generally by the reference numeral 132 and includes an infrared emitting LED 134 as the operative element thereof.

Also embodied in the program carried in the on board microprocessor memory is an inertia compensation means for response to the inertia of the material being introduced to the chamber. This arrangement generally times the interval between the generation of the respective warning and measurement signals mentioned hereinabove and determines therefrom the inertia or rate of introduction of material into the chamber. This may be utilized for producing an inertia compensation signal similar to the temperature compensation signal to adjust or vary the readout or moisture value determined in response to the measurement signal in accordance with the variation in the measured inertia from some predetermined reference value.

Referring to FIG. 6, suitable operator accessible switch means or other suitable signaling means 136, 138 are also provided for accomplishing other operations in accordance with the preferred form of the invention illustrated herein. Preferably, these buttons, which in FIG. 6 are marked with upwardly and downwardly pointing arrows, are used to adjust an internal "bias" in the memory data so as to calibrate the apparatus, for example when measuring some known, reference material. Briefly, during the calibration procedure with a known reference sample of material, the operator utilizes the buttons 136 and 138 to adjust the so-called internal bias setting of the measurement calibration data as necessary to obtain the desired upward or downward movement of the measurement read-out displayed in the display panel 130. The respective buttons 136 and 138 can also be utilized to select from a predetermined list of different materials, and preferably different agricultural grains, for which the instrument contains calibration data suitable for moisture measurement in accordance with the invention.

The display panel 130 is preferably an LCD type display which includes three, 7-segment alphanumeric characters and a decimal point. Referring briefly to FIG. 1, the respective up and down adjustment buttons 136, 138 as well as an off/on switch 139 are preferably provided as pressure sensitive-type membrane switches, and their placement is indicated in FIG. 1 by like reference numerals.

Referring briefly to FIG. 3, various additional mechanical and electrical features of the test apparatus 10 are shown from a bottom view. These include the manner in which a plurality of struck out tabs 200, 202 of the wall members 12, 14 are attached with the bottom wall 15. Also illustrated are a pair of electrically conductive strap-like members which electrically connect with selected ones of the struck out tabs 200, 202 and serve to establish electrical connection of the respective walls 12, 14 with the circuit elements or circuit means 20 as illustrated in FIG. 2.

In order to fully illustrate a specific embodiment of the present invention, the following pages contain a program suitable for enabling the microprocessor 125 to carry out the moisture measurement procedure in accordance with the foregoing description.

```
$ TITLE ('GMT II - DENNIS E. GRIM')
$ ROM(LARGE)
$ DEBUG

/**************************************************************/
/*                                                            */
/*                                                            */
/*          COPYRIGHT (c) 1988                                */
/*          DICKEY-john Corporation                           */
/*          Auburn, Illinois                                  */
/*                                                            */
/*                                                            */
/**************************************************************/

/*
    PHASE     Description
    -----     -----------

0         initial
    1         cell empty
    2         cell nearly full
    3         cell full, measuring temperature
    4         cell full, temperature measurement complete
    5         cell full, bias adjustment mode FLAGS.0 - 0 = TRI-GRAIN, 1 = MULTI-GRAIN
    FLAGS.1 - 0 = Fahrenheit, 1 = Centigrade EEPROM usage
    ------------

00H       T_BIAS
    01H       T_BIAS
    02H       T_BIAS
    03H       EMPTY_CELL MSB
    04H       EMPTY_CELL LSB
    05H       EMPTY_CELL MSB
    06H       EMPTY_CELL LSB
    07H       EMPTY_CELL MSB
    08H       EMPTY_CELL LSB
    09H       M_LOWER
    0AH       M_LOWER
    0BH       M_LOWER
    0CH       M_UPPER
```

```
        0DH         M_UPPER
        0EH         M_UPPER
        0FH         BIAS
        10H         BIAS
        11H         BIAS
        12H         TL MSB
        13H         TL LSB
        14H         TL MSB
        15H         TL LSB
        16H         TL MSB
        17H         TL LSB
        18H         FLAGS
        19H         FLAGS
        1AH         FLAGS
        1BH         GRAIN
        1CH         GRAIN
        1DH         GRAIN
        1EH
        1FH
        20H - 2FH   CALIBRATION  1
        30H - 3FH   CALIBRATION  2
        40H - 4FH   CALIBRATION  3
        50H - 5FH   CALIBRATION  4
        60H - 6FH   CALIBRATION  5
        70H - 7FH   CALIBRATION  6
        80H - 8FH   CALIBRATION  7
        90H - 9FH   CALIBRATION  8
        A0H - AFH   CALIBRATION  9
        B0H - BFH   CALIBRATION 10
        C0H - CFH   CALIBRATION 11
        D0H - DFH   CALIBRATION 12
        E0H - EFH
        F0H - FFH
    */

1   1   GMT_1: DO;

/* LITERAL DECLARATIONS */
2   1   DECLARE DCL LITERALLY 'DECLARE';
3   1   DECLARE CARRIAGE_RETURN LITERALLY '0DH';
4   1   DECLARE FALSE LITERALLY '0';
5   1   DECLARE REG LITERALLY 'REGISTER';
6   1   DECLARE TRUE LITERALLY '1';

/* VARIABLE DECLARATIONS */
7   1   DCL BIAS BYTE PUBLIC MAIN;
8   1   DCL BUFFER(34) BYTE IDATA;
9   1   DCL CALIBRATION STRUCTURE (MOISTURE(6) WORD, (TEMP,BIAS,ID,CKSM) BYTE) MAIN;
10  1   DCL DISPLAY(3) BYTE PUBLIC MAIN;
11  1   DCL EMPTY_CELL WORD MAIN;
12  1   DCL FLAGS BYTE MAIN;
13  1   DCL GRAIN BYTE MAIN;
14  1   DCL KEY_TIMER BYTE MAIN;
15  1   DCL M_LOWER BYTE PUBLIC MAIN;
16  1   DCL M_UPPER BYTE PUBLIC MAIN;
17  1   DCL N BYTE MAIN;
18  1   DCL ONE_SECOND BYTE MAIN;
```

```
19  1         DCL PHASE BYTE MAIN;
20  1         DCL POWER BYTE MAIN;
21  1         DCL RESULT WORD PUBLIC MAIN;
22  1         DCL SCRATCH WORD PUBLIC MAIN;
23  1         DCL T_BIAS BYTE PUBLIC MAIN;
24  1         DCL T_FINAL BYTE PUBLIC MAIN;
25  1         DCL TEMP(11) BYTE MAIN;
26  1         DCL TEMP_COUNT BYTE MAIN;
27  1         DCL TIC BYTE MAIN;
28  1         DCL TIMER BYTE MAIN;
29  1         DCL TOC BYTE MAIN;
30  1         DCL TL WORD PUBLIC MAIN;

/* FLAGS */
31  1         DCL ACK BIT PUBLIC MAIN;
32  1         DCL BLANK BIT PUBLIC MAIN;
33  1         DCL CELL_PENDING BIT MAIN;
34  1         DCL DEC BIT MAIN;
35  1         DCL ENTER BIT MAIN;
36  1         DCL FAIL BIT PUBLIC MAIN;
37  1         DCL INC BIT MAIN;
38  1         DCL KEY_DOWN BIT MAIN;
39  1         DCL LOOP BIT MAIN;
40  1         DCL MOISTURE_LIMIT BIT MAIN;
41  1         DCL OPEN BIT MAIN;
42  1         DCL POINT BIT PUBLIC MAIN;
43  1         DCL POWER_DOWN BIT MAIN;
44  1         DCL SUSPEND BIT MAIN;
45  1         DCL TEMP_CHECK BIT MAIN;
46  1         DCL TEMP_ENABLED BIT MAIN;
47  1         DCL TEMP_ERROR BIT MAIN;
48  1         DCL TEMP_LIMIT BIT MAIN;
49  1         DCL TEMP_PENDING BIT MAIN;
50  1         DCL TEMP_VALID BIT MAIN;
51  1         DCL UPDATE BIT PUBLIC MAIN;

/* SPECIAL FUNCTION REGISTER DECLARATIONS */
52  1         DCL P0     BYTE AT (080H) REG;  /* PORT 0 */
53  1         DCL PCON   BYTE AT (087H) REG;  /* POWER CONTROL REGISTER */
54  1         DCL TMOD   BYTE AT (089H) REG;  /* TIMER MODIFICATION */
55  1         DCL TL0    BYTE AT (08AH) REG;  /* TIMER 0 LSB */
56  1         DCL TL1    BYTE AT (08BH) REG;  /* TIMER 1 LSB */
57  1         DCL TH0    BYTE AT (08CH) REG;  /* TIMER 0 MSB */
58  1         DCL TH1    BYTE AT (08DH) REG;  /* TIMER 1 MSB */
59  1         DCL P1     BYTE AT (090H) REG;  /* PORT 1 */
60  1         DCL SCON   BYTE AT (098H) REG;  /* SERIAL CONTROL */
61  1         DCL SBUF   BYTE AT (099H) REG;  /* SERIAL BUFFER */
62  1         DCL P2     BYTE AT (0A0H) REG;  /* PORT 2 */
63  1         DCL P3     BYTE AT (0B0H) REG;  /* PORT 3 */
64  1         DCL T2CON  BYTE AT (0C8H) REG;  /* TIMER 2 CONTROL */
65  1         DCL RCAP2L BYTE AT (0CAH) REG;  /* TIMER 2 CAPTURE REGISTER LSB */
66  1         DCL RCAP2H BYTE AT (0CBH) REG;  /* TIMER 2 CAPTURE REGISTER MSB */
67  1         DCL TL2    BYTE AT (0CCH) REG;  /* TIMER 2 LSB */
68  1         DCL TH2    BYTE AT (0CDH) REG;  /* TIMER 2 MSB */

69  1         DCL V_TEMP BIT AT (080H) REG;  /* P0.0 (0 = TEMP OSC VCC ON) */
70  1         DCL FLOAT  BIT AT (081H) REG;  /* P0.1 (0 = FLOAT SWITCH CLOSED) */
```

```
71  1       DCL UP      BIT AT (082H) REG;   /* P0.2 (0 = UP SWITCH CLOSED) */
72  1       DCL BP      BIT AT (083H) REG;   /* P0.3 (LCD BACKPLANE) */
73  1       DCL SDA     BIT AT (084H) REG;   /* P0.4 (EEPROM SERIAL DATA) */
74  1       DCL V_CELL  BIT AT (085H) REG;   /* P0.5 (0 = CELL OSC VCC ON) */
75  1       DCL SCL     BIT AT (086H) REG;   /* P0.6 (EEPROM SERIAL CLOCK) */
76  1       DCL DOWN    BIT AT (087H) REG;   /* P0.7 (0 = DOWN SWITCH CLOSED) */
77  1       DCL IT0     BIT AT (088H) REG;   /* EXTERNAL INTERRUPT 0 TYPE FLAG */
78  1       DCL IE0     BIT AT (089H) REG;   /* EXTERNAL INTERRUPT 0 EDGE FLAG */
79  1       DCL TR0     BIT AT (08CH) REG;   /* TIMER 0 RUN/STOP */
80  1       DCL TR1     BIT AT (08EH) REG;   /* TIMER 1 RUN/STOP */
81  1       DCL RI      BIT AT (098H) REG;   /* RECEIVE INTERRUPT FLAG */
82  1       DCL EX0     BIT AT (0A8H) REG;   /* EXT INTERRUPT 0 ENABLE/DISABLE */
83  1       DCL ET0     BIT AT (0A9H) REG;   /* TIMER 0 INTERRUPT ENABLE/DISABLE */
84  1       DCL ET1     BIT AT (0ABH) REG;   /* TIMER 1 INTERRUPT ENABLE/DISABLE */
85  1       DCL ES      BIT AT (0ACH) REG;   /* SERIAL INTERRUPT ENABLE/DISABLE */
86  1       DCL ET2     BIT AT (0ADH) REG;   /* TIMER 2 INTERRUPT ENABLE/DISABLE */
87  1       DCL TRIP    BIT AT (0B2H) REG;   /* P3.2 (0 = TRIP SWITCH CLOSED) */
88  1       DCL PX0     BIT AT (0B8H) REG;   /* External interrupt 0 priority */
89  1       DCL PT2     BIT AT (0BDH) REG;   /* Timer 2 interrupt priority */
90  1       DCL TR2     BIT AT (0CAH) REG;   /* TIMER 2 RUN/STOP */

/* Copyright message. */
91  1       DCL COPYRIGHT(*) BYTE CONSTANT
                ('COPYRIGHT (c) 1988, DICKEY-john Corporation, Auburn, Illinois');

/* LCD right digit (DISPLAY(0)) segment table. */
92  1       DCL TABLE_1 (20) STRUCTURE (PORT(3) BYTE) CONSTANT
            /* PORT         1        2        3      */
            /* BIT       76543210 76543210 76543210  */
            /* SEGMENT    GFABED      C             */
                        (00011111B,10000000B,00000000B,  /* 0 */
                         00000100B,10000000B,00000000B,  /* 1 */
                         00101111B,00000000B,00000000B,  /* 2 */
                         00101101B,10000000B,00000000B,  /* 3 */
                         00110100B,10000000B,00000000B,  /* 4 */
                         00111001B,10000000B,00000000B,  /* 5 */
                         00111011B,10000000B,00000000B,  /* 6 */
                         00001100B,10000000B,00000000B,  /* 7 */
                         00111111B,10000000B,00000000B,  /* 8 */
                         00111101B,10000000B,00000000B,  /* 9 */
                         00111110B,10000000B,00000000B,  /* A */
                         00110011B,10000000B,00000000B,  /* b */
                         00011011B,00000000B,00000000B,  /* C */
                         00100111B,10000000B,00000000B,  /* d */
                         00111011B,00000000B,00000000B,  /* E */
                         00111010B,00000000B,00000000B,  /* F */
                         00000000B,00000000B,00000000B,  /* . */
                         00000001B,00000000B,00000000B,  /* - */
                         00100000B,00000000B,00000000B,  /* - */
                         00001000B,00000000B,00000000B); /* - */

/* LCD middle digit (DISPLAY(1)) segment table. */
93  1       DCL TABLE_2 (20) STRUCTURE (PORT(3) BYTE) CONSTANT
            /* PORT         1        2        3      */
            /* BIT       76543210 76543210 76543210  */
            /* SEGMENT    AB       EG       DC    F  */
                        (11000000B,01000011B,00000010B,  /* 0 */
```

```
                    01000000B,00000001B,00000000B,  /* 1 */
                    11000000B,01100010B,00000000B,  /* 2 */
                    11000000B,00100011B,00000000B,  /* 3 */
                    01000000B,00100001B,00000010B,  /* 4 */
                    10000000B,00100011B,00000010B,  /* 5 */
                    10000000B,01100011B,00000010B,  /* 6 */
                    11000000B,00000001B,00000000B,  /* 7 */
                    11000000B,01100011B,00000010B,  /* 8 */
                    11000000B,00100011B,00000010B,  /* 9 */
                    11000000B,01100001B,00000010B,  /* A */
                    00000000B,01100011B,00000010B,  /* b */
                    10000000B,01000010B,00000010B,  /* C */
                    01000000B,01100011B,00000000B,  /* d */
                    10000000B,01100010B,00000010B,  /* E */
                    10000000B,01100000B,00000010B,  /* F */
                    00000000B,00000000B,00000000B,  /*   */
                    00000000B,00000010B,00000000B,  /* - */
                    00000000B,00100000B,00000000B,  /* - */
                    10000000B,00000000B,00000000B); /* - */

/* LCD (DISPLAY(2)) segment table. */
94   1  DCL TABLE_3 (20) STRUCTURE (PORT(3) BYTE) CONSTANT
        /* PORT            1        2        3     */
        /* BIT          76543210 76543210 76543210 */
        /* SEGMENT               CDE      GF AB    */
                    (00000000B,00011100B,01011000B,  /* 0 */
                    00000000B,00010000B,00001000B,   /* 1 */
                    00000000B,00001100B,10011000B,   /* 2 */
                    00000000B,00011000B,10011000B,   /* 3 */
                    00000000B,00010000B,11001000B,   /* 4 */
                    00000000B,00011000B,11010000B,   /* 5 */
                    00000000B,00011100B,11010000B,   /* 6 */
                    00000000B,00010000B,00011000B,   /* 7 */
                    00000000B,00011100B,11011000B,   /* 8 */
                    00000000B,00011000B,11011000B,   /* 9 */
                    00000000B,00010100B,11011000B,   /* A */
                    00000000B,00011100B,11000000B,   /* b */
                    00000000B,00001100B,01010000B,   /* C */
                    00000000B,00011100B,10001000B,   /* d */
                    00000000B,00001100B,11010000B,   /* E */
                    00000000B,00000100B,11010000B,   /* F */
                    00000000B,00000000B,00000000B,   /* . */
                    00000000B,00001000B,00000000B,   /* - */
                    00000000B,00000000B,10000000B,   /* - */
                    00000000B,00000000B,00010000B);  /* - */

/* Temperature count to degrees fahrenheit conversion table. */
95   1  DCL T(9) STRUCTURE (X WORD,Y WORD) CONSTANT
            /* The TEMPERATURE procedure assumes a nine point table where
               the X interval does not exceed 9 bits and the Y interval does
               not exceed 7 bits. */
            /* F (Hz)*.016,T (F)*8 */
          ( 131,  83,
            187, 198,
            266, 314,
            376, 429,
            528, 544,
```

```
                              734, 659,
                             1005, 774,
                             1347, 890,
                             1758,1005);

/* Temperature correction knee point table. */
96    1     DCL KNEE_TBL(16) WORD CONSTANT
            /* The knee point is specified by the upper four bits of the grain
               calibration temperature constant. */
              (100,   /* 0 - 10.0 */
               120,   /* 1 - 12.0 */
               130,   /* 2 - 13.0 */
               140,   /* 3 - 14.0 */
               150,   /* 4 - 15.0 */
               160,   /* 5 - 16.0 */
               170,   /* 6 - 17.0 */
               180,   /* 7 - 18.0 */
               200,   /* 8 - 20.0 */
               220,   /* 9 - 22.0 */
               240,   /* A - 24.0 */
               250,   /* B - 25.0 */
               260,   /* C - 26.0 */
               280,   /* D - 28.0 */
               300,   /* E - 30.0 */
               320);  /* F - 32.0 */

/* Temperature correction slope table. */
97    1     DCL SLOPE_TBL(16) BYTE CONSTANT
            /* The slope is specified by the lower four bits of the grain
               calibration temperature constant. */
            /* Table values are -(SLOPE * 2^14) for temperature in degrees F. */
            /* WARNING! Table entry must not exceed 127. */
            /* slope       F      C    */
              (036,  /* 0  .0022  .0040 */
               046,  /* 1  .0028  .0050 */
               048,  /* 2  .0029  .0053 */
               052,  /* 3  .0032  .0057 */
               055,  /* 4  .0033  .0060 */
               059,  /* 5  .0036  .0065 */
               062,  /* 6  .0038  .0068 */
               064,  /* 7  .0039  .0070 */
               070,  /* 8  .0043  .0077 */
               073,  /* 9  .0044  .0080 */
               082,  /* A  .0050  .0090 */
               090,  /* B  .0055  .0099 */
               100,  /* C  .0061  .0110 */
               109,  /* D  .0067  .0120 */
               118,  /* E  .0072  .0130 */
               127); /* F  .0078  .0140 */

/* Assembly language routines.  See module GMT_2. */

98    2     CD_NORMAL: PROCEDURE WORD EXTERNAL;
99    2     END;
```

```
100  2      CD_RATIO: PROCEDURE WORD EXTERNAL USING 2;
101  2      END;

102  2      LCD_DRIVE: PROCEDURE EXTERNAL USING 1;
103  2      END;
104  2      OFFSET: PROCEDURE BYTE EXTERNAL;
105  2      END;

106  2      READ: PROCEDURE (SOURCE,DESTINATION,COUNT) EXTERNAL;
            /* Read data from the X2402 EEPROM. */
107  2        DCL SOURCE BYTE MAIN;
108  2        DCL DESTINATION BYTE MAIN;
109  2        DCL COUNT BYTE MAIN;
110  2      END;

111  2      SLOPE: PROCEDURE BYTE EXTERNAL;
112  2      END;

113  2      WRITE: PROCEDURE (PAGE,SOURCE,DESTINATION) EXTERNAL;
            /* Write data to the X2402 EEPROM. */
114  2        DCL PAGE BIT MAIN;
115  2        DCL SOURCE BYTE MAIN;
116  2        DCL DESTINATION BYTE MAIN;
117  2      END;

118  2      MULTI_GRAIN: PROCEDURE BIT;
            /* Return the state of the MULTI_GRAIN flag. */
119  2        IF (FLAGS AND 1) = 1 THEN RETURN TRUE;
121  2        ELSE RETURN FALSE;
122  2      END;

123  2      CENTIGRADE: PROCEDURE BIT;
            /* Return the state of the CENTIGRADE flag. */
124  2        IF (FLAGS AND 2) = 2 THEN RETURN TRUE;
126  2        ELSE RETURN FALSE;
127  2      END;

128  2      CHECKSUM: PROCEDURE BYTE;
129  2        DCL SUM BYTE MAIN;
130  2        DCL CAL(16) BYTE AT (.CALIBRATION);
131  2        DCL I BYTE MAIN;

132  2        SUM = CAL(0);
133  3        DO I = 1 TO 15;
134  3          SUM = SUM + CAL(I);
135  3        END;
136  2        RETURN SUM;
137  2      END;

138  2      CONVERT: PROCEDURE;
            /* Convert display symbol numbers to segment data. */
139  2        DCL I BYTE MAIN;
140  2        DCL SEG(3) BYTE MAIN;
```

```
                /* Convert symbols to segment data. */
141   3         DO I = 0 TO 2;
142   3           SEG(I) = TABLE_1(DISPLAY(0)).PORT(I) OR
                           TABLE_2(DISPLAY(1)).PORT(I) OR
143   3         END;
                /* Copy segment data to display buffer. */
144   3         DO I = 0 TO 2;
145   3           DISPLAY(I) = SEG(I);
146   3         END;
                /* Set the display update flag. */
147   2         UPDATE = TRUE;
148   2       END;

149   2       DISPLAY_CALIBRATION_BIAS: PROCEDURE;
150   2         DCL N BYTE MAIN;

151   2         N = CALIBRATION.BIAS;
152   2         IF N > 7FH THEN
153   3         DO;
154   3           N = (NOT N) + 1;
155   3           DISPLAY(2) = 18;
156   3         END;
157   2         ELSE DISPLAY(2) = 16;
158   2         DISPLAY(1) = N / 10;
159   2         DISPLAY(0) = N MOD 10;
160   2         POINT = TRUE;
161   2         CALL CONVERT;
162   2       END;

163   2       DISPLAY_ERROR: PROCEDURE (NUMBER);
164   2         DCL NUMBER BYTE MAIN;

165   2         DISPLAY(2) = 18;
166   2         DISPLAY(1) = NUMBER;
167   2         DISPLAY(0) = 18;
168   2         POINT = FALSE;
169   2         CALL CONVERT;
170   2       END;

171   2       DISPLAY_GRAIN: PROCEDURE;
172   2         DCL SYMBOL BYTE MAIN;

173   2         DISPLAY(1) = 16;
174   2         IF MULTI_GRAIN THEN
175   2           IF GRAIN < 10 THEN
176   2             IF GRAIN = 0 THEN DISPLAY(2) = 12;
178   2             ELSE DISPLAY(2) = GRAIN;
179   2           ELSE
                   DO;
180   3             DISPLAY(2) = 1;
181   3             DISPLAY(1) = GRAIN - 10;
182   3           END;
183   2         ELSE
                   DO CASE GRAIN;
184   3           DISPLAY(2) = 12;
185   3           DISPLAY(2) = 17;
186   3           DISPLAY(2) = 18;
187   3           DISPLAY(2) = 19;
```

```
188  3        END;
189  2        IF PHASE = 1 THEN DISPLAY(0) = 17;
191  2        ELSE DISPLAY(0) = 19;
192  2        POINT = FALSE;
193  2        CALL CONVERT;
194  2     END;

195  2     DISPLAY_ID: PROCEDURE;
196  2        DCL N BYTE MAIN;

197  2        N = CALIBRATION.ID;
198  2        DISPLAY(2) = N / 100;
199  2        N = N MOD 100;
200  2        DISPLAY(1) = N / 10;
201  2        DISPLAY(0) = N MOD 10;
202  2        POINT = FALSE;
203  2        CALL CONVERT;
204  2     END;

205  2     DISPLAY_RESULT: PROCEDURE;
206  2        DCL N WORD MAIN;
207  2        DCL BIAS WORD MAIN;

208  2        IF GRAIN = 0 THEN
209  2           N = RESULT + 500;
210  2        ELSE
                DO;
211  3           BIAS = CALIBRATION.BIAS;
212  3           IF BIAS > 7FH THEN BIAS = 0FF00H OR BIAS;
214  3           N = RESULT + BIAS;
                 /* Clip result at 0. */
215  3           IF N > 7FFFH THEN N = 0;
217  3        END;
              /* Clip result at 99.9. */
218  2        IF N > 999 THEN N = 999;
220  2        IF N / 100 > 0 THEN DISPLAY(2) = N / 100;
222  2        ELSE DISPLAY(2) = 16;
223  2        N = N MOD 100;
224  2        DISPLAY(1) = N / 10;
225  2        DISPLAY(0) = N MOD 10;
226  2        POINT = TRUE;
227  2        CALL CONVERT;
228  2     END;

229  2     DISPLAY_SYMBOL: PROCEDURE (SYMBOL);
              /* Load the same symbol in all three display positions. */
              /* The decimal point is normally off. */
230  2        DCL SYMBOL BYTE MAIN;

231  2        DISPLAY(2) = SYMBOL;
232  2        DISPLAY(1) = SYMBOL;
233  2        DISPLAY(0) = SYMBOL;
              /* Turn on the decimal point for the display test (88.8). */
234  2        IF SYMBOL = 8 THEN POINT = TRUE;
236  2        ELSE POINT = FALSE;
237  2        CALL CONVERT;
238  2     END;
```

```
239  2        DISPLAY_SAMPLE_TEMPERATURE: PROCEDURE;
240  2          DCL N BYTE MAIN;

/* T_FINAL is temperature * 2^1. */
241  2          IF CENTIGRADE THEN
242  3            DO;
                    /* Fahrenheit to Centigrade conversion. */
243  3              N = (DOUBLE(T_FINAL-64)*5)/9;
                    /* Round temperature to to units resolution. */
244  3              N = SHR(N+1,1);
245  3              IF N > 7FH THEN
246  4                DO;
247  4                  N = (NOT N) + 1;
248  4                  DISPLAY(2) = 18;
249  4                END;
250  3              ELSE DISPLAY(2) = 16;
251  3              DISPLAY(1) = N / 10;
252  3              IF DISPLAY(1) = 0 THEN DISPLAY(1) = 16;
254  3              DISPLAY(0) = N MOD 10;
255  3            END;
256  2          ELSE
                  DO;
                    /* Round temperature to units resolution. */
257  3              N = SHR(T_FINAL+1,1);
258  3              DISPLAY(2) = N / 100;
259  3              N = N MOD 100;
260  3              DISPLAY(1) = N / 10;
261  3              DISPLAY(0) = N MOD 10;
262  3              IF DISPLAY(2) = 0 THEN
263  4                DO;
264  4                  DISPLAY(2) = 16;
265  4                  IF DISPLAY(1) = 0 THEN DISPLAY(1) = 16;
267  4                END;
268  3            END;
269  2          POINT = FALSE;
270  2          CALL CONVERT;
271  2        END;

272  2        IDLE: PROCEDURE;
                /* Activate the IDLE mode. */
273  2          PCON = 1;
274  2        END;

275  2        MOISTURE: PROCEDURE;
                /* Convert RESULT from chart data to moisture. */
276  2          DCL I BYTE MAIN;
277  2          DCL (X1,Y1,X2,Y2) WORD MAIN;

278  3          DO I = 0 TO 4;
279  3            X1 = SHR(CALIBRATION.MOISTURE(I) AND 0FE00H,7);
280  3            Y1 = CALIBRATION.MOISTURE(I) AND 1FFH;
281  3            X2 = SHR(CALIBRATION.MOISTURE(I+1) AND 0FE00H,7);
282  3            Y2 = CALIBRATION.MOISTURE(I+1) AND 1FFH;
                  /* WARNING!: The X and Y differences must not exceed 8 bits. */
283  3            IF RESULT < X2 THEN
284  4              DO;
285  4                IF RESULT + 255 < X1 THEN RESULT = 0;
287  4                ELSE IF RESULT < X1 THEN
```

```
288  5           DO;
289  5             RESULT = (((X1-RESULT)*(Y2-Y1))/(X2-X1));
290  5             IF RESULT < Y1 THEN RESULT = Y1 - RESULT;
292  5             ELSE RESULT = 0;
293  5           END;
294  4         ELSE RESULT = Y1+(((RESULT-X1)*(Y2-Y1))/(X2-X1));
295  4         I = 4;
296  4       END;
297  3     ELSE IF I = 4 THEN
298  4       DO;
299  4         IF RESULT > X2 + 255 THEN
300  4           RESULT = 0;
301  4         ELSE
                  RESULT = Y2+(((RESULT-X2)*(Y2-Y1))/(X2-X1));
302  4       END;
303  3     END;
304  2   END;

305  2   PREDICT: PROCEDURE BYTE USING 2;
         /* RETURN TEMP(N-10)+1.5*(TEMP(N)-TEMP(N-10)) */
306  2     DCL I BYTE MAIN;
307  2     DCL S WORD MAIN;
308  2     DCL L BYTE MAIN;

309  2     IF N = 10 THEN I = 0;
311  2     ELSE I = N + 1;
312  2     IF TEMP(N) > TEMP(I) THEN
313  3       DO;
             /* NOTE: OCH = 1.5 * 2^3 */
314  3         S = TEMP(I)+SHR((DOUBLE(TEMP(N)-TEMP(I))*OCH)+4,3);
             /* Clip the predicted temperature at the temp table maximum. */
315  3         L = SHR(T(8).Y+2,2);
316  3         IF S > L THEN S = L;
318  3       END;
319  2     ELSE
             DO;
             /* NOTE: OCH = 1.5 * 2^3 */
320  3         S = SHR((DOUBLE(TEMP(I)-TEMP(N))*OCH)+4,3);
             /* Clip at 0 to avoid negatives. */
321  3         IF S > TEMP(I) THEN S = 0;
323  3         ELSE S = TEMP(I) - S;
             /* Clip the predicted temperature at the temp table minimum. */
324  3         L = SHR(T(0).Y+2,2);
325  3         IF S < L THEN S = L;
327  3       END;
328  2     RETURN S;
329  2   END;

330  2   SUSPEND_DISPLAY: PROCEDURE;
         /* Suspend display operations. */
331  2     BLANK = TRUE;
332  3     DO WHILE BLANK;
333  3       CALL IDLE;
334  3     END;
335  2     SUSPEND = TRUE;
336  2   END;
```

```
337   2       RETRIEVE_CALIBRATION: PROCEDURE;
338   2           DCL LOCATION BYTE MAIN;

339   2           CALL SUSPEND_DISPLAY;
                  /* Read the calibration. */
340   2           LOCATION = GRAIN * 16 + 16;
341   2           FAIL = FALSE;
342   2           CALL READ (LOCATION,.CALIBRATION,16);
                  /* Do not use this calibration if there were any problems
                     reading the EEPROM. */
343   2           IF FAIL THEN CALIBRATION.ID = 0;
                  /* Do not use this calibration if the checksum is bad. */
345   2           IF (CHECKSUM <> 55H) THEN CALIBRATION.ID = 0;
                  /* Restore the display. */
347   2           SUSPEND = FALSE;
348   2       END;

349   2       RETRIEVE_BYTE: PROCEDURE (LOCATION) BYTE;
350   2           DCL LOCATION BYTE MAIN;
351   2           DCL BUFFER(3) BYTE MAIN;
352   2           DCL DATA BYTE MAIN;

353   2           CALL SUSPEND_DISPLAY;
354   2           CALL READ (LOCATION,.BUFFER,3);
355   2           IF BUFFER(0) = BUFFER(1) THEN DATA = BUFFER(0);
357   2           ELSE IF BUFFER(1) = BUFFER(2) THEN DATA = BUFFER(1);
359   2           ELSE IF BUFFER(2) = BUFFER(0) THEN DATA = BUFFER(2);
361   2           ELSE FAIL = TRUE;
362   2           SUSPEND = FALSE;
363   2           RETURN DATA;
364   2       END;

365   2       RETRIEVE_WORD: PROCEDURE (LOCATION) WORD;
366   2           DCL LOCATION BYTE MAIN;
367   2           DCL BUFFER(3) WORD MAIN;
368   2           DCL DATA WORD MAIN;

369   2           CALL SUSPEND_DISPLAY;
370   2           CALL READ (LOCATION,.BUFFER,6);
371   2           IF BUFFER(0) = BUFFER(1) THEN DATA = BUFFER(0);
373   2           ELSE IF BUFFER(1) = BUFFER(2) THEN DATA = BUFFER(1);
375   2           ELSE IF BUFFER(2) = BUFFER(0) THEN DATA = BUFFER(2);
377   2           ELSE FAIL = TRUE;
378   2           SUSPEND = FALSE;
379   2           RETURN DATA;
380   2       END;

381   2       STORE_CALIBRATION_BIAS: PROCEDURE;
382   2           DCL LOCATION BYTE MAIN;

383   2           CALL SUSPEND_DISPLAY;
384   2           LOCATION = GRAIN * 16 + 16;
385   2           CALL WRITE (0,.CALIBRATION.BIAS,LOCATION+13);
386   2           SUSPEND = FALSE;
387   2       END;

388   2       STORE_CALIBRATION_CKSM: PROCEDURE;
```

```
389   2         DCL LOCATION BYTE MAIN;

390   2         CALL SUSPEND_DISPLAY;
391   2         LOCATION = GRAIN * 16 + 16;
392   2         CALL WRITE (0,.CALIBRATION.CKSM,LOCATION+15);
393   2         SUSPEND = FALSE;
394   2       END;

395   2     STORE_BYTE: PROCEDURE (DATA,LOCATION);
396   2         DCL DATA BYTE MAIN;
397   2         DCL LOCATION BYTE MAIN;
398   2         DCL I BYTE MAIN;

399   2         CALL SUSPEND_DISPLAY;
400   3         DO I = 1 TO 3;
401   3           CALL WRITE (0,.DATA,LOCATION);
402   3           LOCATION = LOCATION + 1;
403   3         END;
404   2         SUSPEND = FALSE;
405   2       END;

406   2     STORE_WORD: PROCEDURE (DATA,LOCATION);
407   2         DCL DATA WORD MAIN;
408   2         DCL LOCATION BYTE MAIN;
409   2         DCL I BYTE MAIN;

410   2         CALL SUSPEND_DISPLAY;
411   3         DO I = 1 TO 3;
412   3           CALL WRITE (0,.DATA,LOCATION);
413   3           CALL WRITE (0,.DATA+1,LOCATION+1);
414   3           LOCATION = LOCATION + 2;
415   3         END;
416   2         SUSPEND = FALSE;
417   2       END;

418   2     TEMPERATURE: PROCEDURE BYTE USING 2;
419   2         DCL I BYTE MAIN;
420   2         DCL X WORD MAIN;

421   2         X = SHL(DOUBLE(TH1),8) OR TL1;
              /* WARNING!: X - X(I) must not exceed 9 bits and Y(I+1) - Y(I)
                 must not exceed 7 bits. */
422   3         DO I = 0 TO 7;
423   3           IF X < T(I+1).X THEN
424   4             DO;
425   4               IF X < T(0).X THEN
426   4                 IF TEMP_CHECK THEN TEMP_ERROR = TRUE;
428   4                 ELSE X = T(0).Y;
429   4               ELSE
                        X = T(I).Y+(((X-T(I).X)*(T(I+1).Y-T(I).Y))/(T(I+1).X-T(I).X));
430   4               I = 7;
431   4             END;
432   3           ELSE
                    IF I = 7 THEN
433   3               IF TEMP_CHECK THEN TEMP_ERROR = TRUE;
435   3               ELSE X = T(8).Y;
436   3         END;
```

```
437   2        TEMP_CHECK = FALSE;
               /* ROUND TO NEAREST 1/2 DEGREE F. */
438   2        RETURN SHR(X+2,2);
439   2     END;

440   2     TEMPERATURE_CORRECTION: PROCEDURE;
441   2        DCL KNEE WORD MAIN;
442   2        DCL SLOPE BYTE MAIN;
443   2        DCL C WORD MAIN;

/* for %Ma <  %Mk   %M = %Ma + (T - 68) * %Ma * S
                  for %Ma >= %Mk   %M = %Ma + (T - 68) * %Mk * S
                  where %Ma = uncorrected moisture
                        %Mk = knee point moisture
                        T   = sample temperature
                        S   = correction slope */
444   2        KNEE = KNEE_TBL(SHR(CALIBRATION.TEMP,4));
445   2        SLOPE = SLOPE_TBL(CALIBRATION.TEMP AND 0FH);
446   2        IF RESULT < KNEE THEN
447   2           C = RESULT * SLOPE;
448   2        ELSE
                  C = KNEE * SLOPE;
               /* ROUND TO 9 BITS. */
449   2        C = SHR(C+64,7);
               /*NOTE : T_FINAL = TEMP * 2^1
                        136 = 68 * 2^1 */
450   2        IF T_FINAL > 136 THEN
451   2           RESULT = RESULT - SHR((T_FINAL-136)*C+128,8);
452   2        ELSE
                  RESULT = RESULT + SHR((136-T_FINAL)*C+128,8);
453   2     END;

454   2     TERMINATE: PROCEDURE (N);
455   2        DCL N BYTE MAIN;

456   2        CALL DISPLAY_ERROR (N);
457   2        POWER = 5;
458   3        DO WHILE 1;
459   3           CALL IDLE;
460   3        END;
461   2     END;

462   2     UPDATE_CALIBRATION_CKSM: PROCEDURE;
463   2        DCL SUM BYTE MAIN;
464   2        DCL CAL(16) BYTE AT (.CALIBRATION);
465   2        DCL I BYTE MAIN;

466   2        SUM = CAL(0);
467   3        DO I = 1 TO 14;
468   3           SUM = SUM + CAL(I);
469   3        END;
470   2        CALIBRATION.CKSM = 55H - SUM;
471   2     END;

472   2     EXTERNAL_0: PROCEDURE INTERRUPT 0 USING 2;
```

```
                /* External interrupt 0 - high priority */
                /* This interrupt is generated when the trip switch closes
                    or when bit IE0 in TCON is set by software. The service
                    routine initiates a cell measurement. */

/* Disable the trip switch interrupt. */
473    2        EX0 = 0;
                /* Abort a possible in-progress temperature measurement. */
474    2        TR1 = 0;
475    2        TR2 = 0;
476    2        V_TEMP = 1;
                /* Turn on the cell oscillator. */
477    2        V_CELL = 0;
                /* Wait approximately 400 microseconds for the cell oscillator to
                    stabilize. */
478    2        CALL TIME (4);
                /* Configure timer 1 as a 16 bit counter. */
479    2        TMOD = 51H;
480    2        TH1 = 0;
481    2        TL1 = 0;
                /* Configure timer 2 to generate an interrupt in 16 ms. */
                /* NOTE: Allow for the interrupt handler time. */
482    2        T2CON = 0;
483    2        TH2 = 0C6H;
484    2        TL2 = 0C8H;
485    2        ET2 = 1;
486    2        TR2 = 1;
                /* Start counting. */
487    2        TR1 = 1;
488    2        END;

489    2        TIMER_0: PROCEDURE INTERRUPT 1 USING 1;
                /* Timer interrupt 0 - low priority */
                /* This interrupt occurs every 8.3 milliseconds. The service
                    routine provides 60 Hz AC drive for the LCD and performs
                    several other functions. */

/* Reload timer 0. NOTE: Allow for the interrupt handler time. */
490    2        TL0 = 03EH;
491    2        TH0 = 0E2H;
                /* Ignore the LCD if display service has been suspended. */
492    2        IF NOT SUSPEND THEN CALL LCD_DRIVE;
                /* Increment the time base. */
494    2        TIMER = TIMER + 1;
                /* Check the one second timer. */
495    2        IF TIMER = ONE_SECOND THEN
496    3        DO;
497    3           ONE_SECOND = TIMER + 120;
                /* Unconditional power down. */
498    3           IF POWER_DOWN THEN
499    4           DO;
500    4              P0 = 0;
501    4              P1 = 0;
502    4              P2 = 0;
503    4              P3 = 0;
504    5              DO WHILE 1;
505    5              END;
```

```
506  4           END;
                 /* Decrement the power timer. */
507  3           IF POWER = 1 THEN POWER_DOWN = TRUE;
509  3           ELSE POWER = POWER - 1;
                 /* Initiate a temperature measurement. */
510  3           IF TEMP_ENABLED THEN TEMP_PENDING = TRUE;
512  3         END;
               /* Start temperature measurement. */
513  2         IF TEMP_PENDING THEN
                 /* Skip if cell or temperature measurement in progress. */
514  2           IF V_CELL AND V_TEMP THEN
515  3             DO;
                   /* Turn on the temperature oscillator. */
516  3             V_TEMP = 0;
                   /* Allow time (approximately 100 microseconds) for
                       the temperature oscillator to start. */
517  3             CALL TIME (1);
                   /* Configure timer 1 as a 16 bit counter. */
518  3             TMOD = 51H;
519  3             TH1 = 0;
520  3             TL1 = 0;
                   /* Configure timer 2 to generate an interrupt in 16 ms. */
                   /* NOTE: Allow for the interrupt handler time. */
521  3             T2CON = 0;
522  3             TH2 = 0C6H;
523  3             TL2 = 0C8H;
524  3             ET2 = 1;
525  3             TR2 = 1;
                   /* Start counting. */
526  3             TR1 = 1;
527  3            END;
               /* Debounce the UP and DOWN buttons. */
528  2         IF KEY_DOWN THEN
529  3          DO;
530  3            IF UP AND DOWN THEN
531  4             DO;
532  4               KEY_DOWN = FALSE;
533  4               KEY_TIMER = 32;
534  4             END;
535  3          END;
536  2         ELSE
                DO;
537  3            IF KEY_TIMER > 0 THEN KEY_TIMER = KEY_TIMER - 1;
539  3            ELSE IF UP = 0 THEN
540  4             DO;
541  4               INC = TRUE;
542  4               KEY_DOWN = TRUE;
543  4             END;
544  3            ELSE IF DOWN = 0 THEN
545  4             DO;
546  4               DEC = TRUE;
547  4               KEY_DOWN = TRUE;
548  4             END;
549  3          END;
550  2         END;

551  2         TIMER_1: PROCEDURE INTERRUPT 3 USING 1;
```

```
                /* Timer 1 interrupt - low priority */
                /* This interrupt occurs if more than 71 milliseconds elapse between
                    the receipt of two consecutive characters on the serial port. */

/* Disable timer 1 interrupt. */
552   2         ET1 = 0;
553   2         TR1 = 0;
                /* Reset the input string pointer. */
554   2         N = 0;
555   2         END;

556   2     SERIAL: PROCEDURE INTERRUPT 4 USING 1;
                /* Serial port interrupt - low priority */
                /* This interrupt is generated when a character has been received
                    at the serial port. */

/* Reset the receive interrupt flag. */
557   2         RI = FALSE;
                /* Configure timer 1 to monitor the time between receipt of characters
                    at the serial port. If the next character is not received within
                    71 milliseconds, clear the input string. */
558   2         TMOD = 11H;
559   2         TH1 = 0;
560   2         TL1 = 0;
561   2         TR1 = 1;
562   2         ET1 = 1;
                /* Get the received character from the serial port. */
563   2         IF OPEN THEN
564   3         DO;
565   3           IF SBUF = CARRIAGE_RETURN THEN
566   3             ENTER = TRUE;
567   3           ELSE
                  DO;
568   4             BUFFER(N) = SBUF;
569   4             IF N < 33 THEN N = N + 1;
571   4           END;
572   3         END;
573   2         ELSE
                  DO CASE N AND 3;
574   3           IF SBUF = '1' THEN N = 1;
576   3           IF SBUF = '2' THEN N = 2;
578   3           ELSE N = 0;
579   3           IF SBUF = '3' THEN N = 3;
581   3           ELSE N = 0;
582   3           IF SBUF = '3' THEN OPEN = TRUE;
584   3           ELSE N = 0;
585   3           END;
586   2         END;

587   2     TIMER_2: PROCEDURE INTERRUPT 5 USING 2;
                /* Timer 2 interrupt - high priority */
                /* Timer 2 is set to roll over in 16 milliseconds when a cell
                    or temperature measurement is started. */
588   2         DCL T_TEMP BYTE MAIN;

/* Stop counting. */
589   2         TR1 = 0;
```

```
                /* Disable timer 2 interrupts. */
590    2        T2CON = 0;
591    2        ET2 = 0;
592    2        IF V_CELL = 0 THEN
593    3        DO;
                   /* Turn off the cell oscillator. */
594    3           V_CELL = 1;
                   /* Unload timer 1. */
595    3           IF RESULT = 0 THEN
                      /* Timer 1 holds the empty cell count. */
596    3              RESULT = SHL(DOUBLE(TH1),8) OR TL1;
597    3           ELSE
                      /* Timer 1 holds the full cell count. */
                      RESULT = CD_RATIO;
598    3           CELL_PENDING = FALSE;
599    3        END;
600    2        ELSE
                DO;
                   /* Turn off the temperature oscillator. */
601    3           V_TEMP = 1;
                   /* Unload timer 1. */
602    3           TEMP(N) = TEMPERATURE;
603    3           IF PHASE = 3 THEN TEMP_COUNT = TEMP_COUNT + 1;
605    3           IF TEMP_VALID THEN
606    4           DO;
                      /* Save the last temperature prediction. */
607    4              T_TEMP = T_FINAL;
                      /* Make a new temperature prediction. */
608    4              T_FINAL = PREDICT;
609    4              IF PHASE = 3 THEN
610    5              DO;
611    5                 IF T_FINAL > T_TEMP THEN
612    5                    T_TEMP = T_FINAL - T_TEMP;
613    5                 ELSE
                            T_TEMP = T_TEMP - T_FINAL;
614    5                 IF (T_TEMP < 2) OR (TEMP_COUNT = 15) THEN
615    6                 DO;
616    6                    TEMP_ENABLED = FALSE;
                            /* Add the temperature bias. */
617    6                    T_FINAL = T_FINAL + T_BIAS;
                            /* Check temperature limits. */
                            /* NOTE: T_FINAL = TEMP * 2^1
                                     64 = 32 * 2^1
                                     220 = 110 * 2^1 */
618    6                    IF T_FINAL < 64 THEN TEMP_LIMIT = TRUE;
620    6                    ELSE IF T_FINAL > 220 THEN TEMP_LIMIT = TRUE;
622    6                 END;
623    5              END;
624    4           END;
625    3           ELSE IF N = 10 THEN
626    4           DO;
627    4              T_FINAL = PREDICT;
628    4              TEMP_VALID = TRUE;
629    4           END;
                   /* Increment the temperature array pointer. */
630    3           IF N = 10 THEN N = 0;
632    3           ELSE N = N + 1;
```

```
633  3          TEMP_PENDING = FALSE;
634  3        END;
635  2     END;

/*** Setup routines. ***/

636  2     DIGIT: PROCEDURE BYTE;
             /* Convert the next character in the buffer to a hex digit and
                increment the buffer pointer. */
637  2       DCL DIGIT BYTE MAIN;

638  2       DIGIT = BUFFER(N);
639  2       N = N + 1;
640  2       IF 2FH < DIGIT AND DIGIT < 3AH THEN RETURN DIGIT - 30H;
642  2       ELSE IF 40H < DIGIT AND DIGIT < 47H THEN RETURN DIGIT - 37H;
644  2       ELSE RETURN 0;
645  2     END;

646  2     HEX_BYTE: PROCEDURE BYTE;
             /* Return the hex byte represented by the next two ASCII
                characters in the buffer. */
647  2       DCL HEX_BYTE BYTE MAIN;

648  2       HEX_BYTE = DIGIT;
649  2       RETURN SHL(HEX_BYTE,4) OR DIGIT;
650  2     END;

651  2     HEX_WORD: PROCEDURE WORD;
             /* Return the hex word represented by the next four ASCII
                characters in the buffer. */
652  2       DCL HEX_WORD WORD MAIN;

653  2       HEX_WORD = DIGIT;
654  2       HEX_WORD = SHL(HEX_WORD,4) OR DIGIT;
655  2       HEX_WORD = SHL(HEX_WORD,4) OR DIGIT;
656  2       RETURN SHL(HEX_WORD,4) OR DIGIT;
657  2     END;

658  2     DISPLAY_BYTE: PROCEDURE (N);
659  2       DCL N BYTE MAIN;

660  2       DISPLAY(2) = 16;
661  2       DISPLAY(1) = SHR(N,4);
662  2       DISPLAY(0) = N AND 0FH;
663  2       POINT = FALSE;
664  2       CALL CONVERT;
665  2     END;

666  2     DISPLAY_COUNT: PROCEDURE (N);
667  2       DCL N WORD MAIN;

/* Display the count. */
668  2       IF DOWN = 0 THEN
               /* Display the 3 LSDs of the count. */
669  2         N = N MOD 1000;
```

```
670  2       ELSE
             /* Display the 3 MSDs of the count. */
             N = N / 10;
671  2       DISPLAY(2) = N / 100;
672  2       N = N MOD 100;
673  2       DISPLAY(1) = N / 10;
674  2       DISPLAY(0) = N MOD 10;
675  2       POINT = FALSE;
676  2       CALL CONVERT;
677  2     END;

678  2     ENABLE_TEMPERATURE: PROCEDURE;
             /* Turn on the temperature oscillator. */
679  2       V_TEMP = 0;
680  2       CALL DISPLAY_SYMBOL (19);
681  2       INC = FALSE;
682  3       DO WHILE NOT INC;
683  3         CALL IDLE;
684  3       END;
             /* Turn off the temperature oscillator. */
685  2       V_TEMP = 1;
686  2       CALL DISPLAY_SYMBOL (18);
687  2     END;

688  2     DISPLAY_TEMPERATURE_COUNT: PROCEDURE;
689  2       DCL COUNT WORD MAIN;

/* Disable the serial interrupt to avoid possible timing problems. */
690  2       ES = FALSE;
             /* Release timer 1 for use in data collection. */
691  2       TR1 = FALSE;
692  2       ET1 = FALSE;
             /* Update the display 8 times a second until the UP button is pressed. */
693  2       TIC = TIMER + 1;
694  2       INC = FALSE;
695  2       LOOP = TRUE;
696  3       DO WHILE LOOP;
697  3         IF TIMER = TIC THEN
698  4         DO;
699  4           TIC = TIMER + 15;
                 /* Measure the cell temperature. */
700  4           N = 0;
701  4           TEMP_VALID = FALSE;
702  4           TEMP_PENDING = TRUE;
703  5           DO WHILE TEMP_PENDING;
704  5             CALL IDLE;
705  5           END;
706  4           CALL DISPLAY_COUNT (SHL(DOUBLE(TH1),8) OR TL1);
707  4         END;
708  3         IF INC THEN LOOP = FALSE;
710  3         IF LOOP THEN CALL IDLE;
712  3       END;
713  2       CALL DISPLAY_SYMBOL (18);
714  2     END;

715  2     DISPLAY_TEMPERATURE: PROCEDURE;
             /* Disable the serial interrupt to avoid possible timing problems. */
```

```
716  2          ES = FALSE;
                /* Release timer 1 for use in data collection. */
717  2          TR1 = FALSE;
718  2          ET1 = FALSE;
                /* Measure the cell temperature. */
719  2          N = 0;
720  2          TEMP_VALID = FALSE;
721  2          TEMP_PENDING = TRUE;
722  3          DO WHILE TEMP_PENDING;
723  3             CALL IDLE;
724  3          END;
                /* Display the temperature. */
725  2          T_FINAL = TEMP(0);
726  2          CALL DISPLAY_SAMPLE_TEMPERATURE;
727  2       END;

728  2       COMPUTE_TEMPERATURE_BIAS: PROCEDURE;
729  2          DCL TARGET BYTE MAIN;

/* Disable the serial interrupt to avoid possible timing problems. */
730  2          ES = FALSE;
                /* Release timer 1 for use in data collection. */
731  2          TR1 = FALSE;
732  2          ET1 = FALSE;
                /* Read the target temperature from the command buffer. */
733  2          N = 1;
734  2          TARGET = HEX_BYTE;
                /* Measure the cell temperature. */
735  2          N = 0;
736  2          TEMP_VALID = FALSE;
737  2.         TEMP_PENDING = TRUE;
738  3          DO WHILE TEMP_PENDING;
739  3.            CALL IDLE;
740  3          END;
                /* Compute and store the tmeperature bias. */
741  2          T_BIAS = TARGET - TEMP(0);
742  2          FAIL = FALSE;
743  2          CALL STORE_BYTE (T_BIAS,00H);
                /* Display the temperature bias. */
744  2          IF FAIL THEN CALL DISPLAY_ERROR (2);
746  2          ELSE CALL DISPLAY_BYTE (T_BIAS);
747  2       END;

748  2       ENABLE_CELL: PROCEDURE;
                /* Turn on the cell oscillator. */
749  2          V_CELL = 0;
750  2          CALL DISPLAY_SYMBOL (19);
751  2          INC = FALSE;
752  3          DO WHILE NOT INC;
753  3             CALL IDLE;
754  3          END;
                /* Turn off the cell oscillator. */
755  2          V_CELL = 1;
756  2          CALL DISPLAY_SYMBOL (18);
757  2       END;

758  2       DISPLAY_CELL_COUNT: PROCEDURE;
```

```
759  2        DCL COUNT WORD MAIN;

/* Disable the serial interrupt to avoid possible timing problems. */
760  2        ES = FALSE;
              /* Release timer 1 for use in data collection. */
761  2        TR1 = FALSE;
762  2        ET1 = FALSE;
              /* Update the display 8 times a second until the UP button is pressed. */
763  2        TIC = TIMER + 1;
764  2        INC = FALSE;
765  2        LOOP = TRUE;
766  3        DO WHILE LOOP;
767  3          IF TIMER = TIC THEN
768  4            DO;
769  4              TIC = TIMER + 15;
                    /* Measure the empty cell. */
770  4              RESULT = 0;
771  4              CELL_PENDING = TRUE;
772  4              EX0 = 1;
773  4              IE0 = 1;
774  5              DO WHILE CELL_PENDING;
775  5                CALL IDLE;
776  5              END;
777  4              CALL DISPLAY_COUNT (SHL(DOUBLE(TH1),8) OR TL1);
778  4            END;
779  3          IF INC THEN LOOP = FALSE;
781  3          IF LOOP THEN CALL IDLE;
783  3        END;
784  2        CALL DISPLAY_SYMBOL (18);
785  2        END;

786  2        NORMALIZE: PROCEDURE;
787  2          DECLARE (CL,CH,TH) WORD MAIN;
                /* SCRATCH is used for parameter passing. */

/* Disable the serial interrupt to avoid possible timing problems. */
788  2          ES = FALSE;
                /* Release timer 1 for use in data collection. */
789  2          TR1 = FALSE;
790  2          ET1 = FALSE;
                /* Get TL from the command buffer. */
791  2          N = 1;
792  2          TL = HEX_WORD;
                /* Get TH from the command buffer. */
793  2          TH = HEX_WORD;
                /* Set lower slope to 1.0. */
794  2          M_LOWER = 80H;
                /* Set upper slope to 1.0. */
795  2          M_UPPER = 80H;
                /* Initial offset is 0. */
796  2          BIAS = 0;
                /* Measure the empty cell. */
797  2          RESULT = 0;
798  2          CELL_PENDING = TRUE;
799  2          EX0 = 1;
800  2          IE0 = 1;
801  3          DO WHILE CELL_PENDING;
```

```
802  3        CALL IDLE;
803  3        END;
804  2     EMPTY_CELL = RESULT;
           /* Low value test capacitor measurement. */
805  2     CALL DISPLAY_SYMBOL (17);
806  2     DEC = FALSE;
807  3     DO WHILE NOT DEC;
808  3        CALL IDLE;
809  3     END;
810  2     CELL_PENDING = TRUE;
811  2     EX0 = 1;
812  2     IE0 = 1;
813  3     DO WHILE CELL_PENDING;
814  3        CALL IDLE;
815  3     END;
816  2     CL = RESULT;
           /* High value test capacitor measurement. */
817  2     CALL DISPLAY_SYMBOL (19);
818  2     RESULT = EMPTY_CELL;
819  2     INC = FALSE;
820  3     DO WHILE NOT INC;
821  3        CALL IDLE;
822  3     END;
823  2     CELL_PENDING = TRUE;
824  2     EX0 = 1;
825  2     IE0 = 1;
826  3     DO WHILE CELL_PENDING;
827  3        CALL IDLE;
828  3     END;
829  2     CH = RESULT;
           /* Compute M_UPPER. */
830  2     RESULT = CH - CL;
831  2     SCRATCH = TH - TL;
832  2     M_UPPER = SLOPE;
           /* Compute the offset. */
833  2     RESULT = CL;
834  2     SCRATCH = TL;
835  2     BIAS = OFFSET;
           /* Compute M_LOWER. */
           /* RESULT = CL and SCRATCH = TL. */
836  2     M_LOWER = SLOPE;
           /* Store the normalization constants. */
837  2     FAIL = FALSE;
838  2     CALL STORE_WORD (EMPTY_CELL,03H);
839  2     CALL STORE_BYTE (M_LOWER,09H);
840  2     CALL STORE_BYTE (M_UPPER,0CH);
841  2     CALL STORE_BYTE (BIAS,0FH);
842  2     CALL STORE_WORD (TL,12H);
           /* Display the setup prompt. */
843  2     IF FAIL THEN CALL DISPLAY_ERROR (2);
845  2     ELSE CALL DISPLAY_SYMBOL (18);
846  2     END;

847  2     DISPLAY_EMPTY_CELL_COUNT: PROCEDURE;
           /* Update the display 8 times a second until the UP button is pressed. */
848  2     TIC = TIMER + 1;
849  2     INC = FALSE;
```

```
850  2        LOOP = TRUE;
851  3        DO WHILE LOOP;
852  3          IF TIMER = TIC THEN
853  4            DO;
854  4              TIC = TIMER + 15;
855  4              CALL DISPLAY_COUNT (EMPTY_CELL);
856  4            END;
857  3          IF INC THEN LOOP = FALSE;
859  3          IF LOOP THEN CALL IDLE;
861  3        END;
862  2        CALL DISPLAY_SYMBOL (18);
863  2      END;

864  2      STORE_CONFIGURATION: PROCEDURE;
            /* Store the unit configuration. */
865  2        N = 1;
866  2        FLAGS = DIGIT;
867  2        GRAIN = 0;
868  2        FAIL = FALSE;
869  2        CALL STORE_BYTE (FLAGS,18H);
870  2        CALL STORE_BYTE (GRAIN,1BH);
            /* Display the configuration flags. */
871  2        IF FAIL THEN CALL DISPLAY_ERROR (2);
873  2        ELSE CALL DISPLAY_BYTE (FLAGS);
874  2      END;

875  2      STORE_CALIBRATION: PROCEDURE;
876  2        DCL I BYTE MAIN;
877  2        DCL CAL(16) BYTE AT (.CALIBRATION);
878  2        DCL LOCATION BYTE MAIN;

/* Get the calibration number from the input buffer. */
879  2        N = 1;
880  2        GRAIN = DIGIT;
881  2        IF 0 < GRAIN AND GRAIN < 13 THEN
882  3          DO;
            /* Convert the ASCII string in the buffer to a calibration. */
883  4            DO I = 0 TO 15;
884  4              CAL(I) = HEX_BYTE;
885  4            END;
            /* Another calibration can be received while this one is being
                saved in the EEPROM. */
886  3            ENTER = FALSE;
887  3            N = 0;
            /* Store calibration in EEPROM. */
888  3            CALL SUSPEND_DISPLAY;
889  3            LOCATION = GRAIN * 16 + 16;
890  3            FAIL = FALSE;
891  3            CALL WRITE (1,.CALIBRATION.MOISTURE(0),LOCATION);
892  3            CALL WRITE (1,.CALIBRATION.MOISTURE(4),LOCATION+8);
893  3            SUSPEND = FALSE;
            /* Display GRAIN. */
894  3            IF FAIL THEN CALL DISPLAY_ERROR (2);
896  3            ELSE CALL DISPLAY_BYTE (GRAIN);
897  3          END;
898  2      END;
```

```
899  2    RUN_CPU: PROCEDURE;
900  2      CALL DISPLAY_SYMBOL (19);
            /* Loop without idle. */
901  2      INC = FALSE;
902  3      DO WHILE NOT INC;
903  3      END;
904  2      CALL DISPLAY_SYMBOL (18);
905  2    END;

906  2    TEST_DISPLAY: PROCEDURE;
907  2      N = 0;
908  2      TIC = TIMER + 1;
909  2      LOOP = TRUE;
910  3      DO WHILE LOOP;
911  3        IF TIMER = TIC THEN
912  4          DO;
913  4            TIC = TIMER + 60;
914  4            IF N = 20 THEN LOOP = FALSE;
916  4            ELSE CALL DISPLAY_SYMBOL (N);
917  4            N = N + 1;
918  4          END;
919  3        IF LOOP THEN CALL IDLE;
921  3      END;
922  2      CALL DISPLAY_SYMBOL (18);
923  2    END;
```

/* Program execution continues here after the reset vector. */

/* X2402 stop condition. */

```
924  1    SCL = 0;
925  1    SDA = 0;
926  1    SCL = 1;
927  1    SCL = 1;
928  1    SCL = 1;
929  1    SCL = 1;
930  1    SCL = 1;
931  1    SDA = 1;
```

/* Initialize variables. */

```
932  1    BLANK = FALSE;
933  1    CELL_PENDING = FALSE;
934  1    ONE_SECOND = 120;
935  1    PHASE = 0;
936  1    POWER = 60;
937  1    POWER_DOWN = FALSE;
938  1    SUSPEND = FALSE;
939  1    TEMP_ENABLED = FALSE;
940  1    TEMP_PENDING = FALSE;
941  1    TIMER = 0;
942  1    UPDATE = FALSE;
```

/* External interrupt 0 is falling edge triggered. */

```
943   1      IT0 = 1;

/* External interrupt 0 and timer interrupt 2 are high priority.
                All other interrupts are low priority. */

944   1      PX0 = 1;
945   1      PT2 = 1;

/* Configure TIMER 0 to generate an interrupt at 8.3 ms (60 Hz) intervals.
                The timer 0 interrupt service routine provides the ac drive for the LCD
                and the timing for most functions. NOTE: Allow time for the interrupt
                handler. */

946   1      TMOD = 1;
947   1      TH0 = 0E2H;
948   1      TL0 = 03EH;
949   1      TR0 = 1;
950   1      ET0 = 1;

/* Globally enable interrupts. */

951   1      ENABLE;

/* If the UP and DOWN buttons are pressed then display the trip
                switch status. Power down in 4.25 minutes. */

952   1      IF (UP OR DOWN) = 0 THEN
953   2        DO;
954   2          POWER = 255;
955   2          TIC = TIMER + 1;
956   3          DO WHILE 1;
957   3            IF TIMER = TIC THEN
958   4              DO;
959   4                TIC = TIMER + 15;
960   4                IF FLOAT = 0 THEN CALL DISPLAY_SYMBOL (19);
962   4                ELSE IF TRIP = 0 THEN CALL DISPLAY_SYMBOL (17);
964   4                ELSE CALL DISPLAY_SYMBOL (18);
965   4              END;
966   3            CALL IDLE;
967   3          END;
968   2        END;

/* Display the test pattern (88.8). */

969   1      CALL DISPLAY_SYMBOL (8);

/* The serial port is used to access the setup routines and is
                configured for 1 start bit, 8 data bits, no parity bit and 1
                stop bit at 1200 bits per second. */

970   1      OPEN = FALSE;
971   1      N = 0;
972   1      RCAP2H = 0FEH;
973   1      RCAP2L = 0E1H;
974   1      T2CON = 24H;
975   1      SCON = 70H;
976   1      ES = TRUE;
```

/* To gain access to the setup routines, the four character access
   code "1233" must be received during this 500 millisecond window. */

```
977   1     TIC = TIMER + 60;
978   1     LOOP = TRUE;
979   2     DO WHILE LOOP;
980   2       IF TIMER = TIC THEN LOOP = FALSE;
982   2       IF LOOP THEN CALL IDLE;
984   2     END;

985   1     IF OPEN THEN
986   2     DO;
              /* The access code has been received. */
987   2       ENTER = FALSE;
              /* Display the command prompt (---). */
988   2       CALL DISPLAY_SYMBOL (18);
              /* Set power down to occur in 4.25 minutes. */
989   2       POWER = 255;
990   2     END;

991   2     DO WHILE OPEN;
              /* The access code has been received.  Monitor the serial port for
                 commands until released by command or until power down. */
992   2       IF ENTER THEN
993   3       DO;
                /* Command processing requested. */
994   3         IF BUFFER(0) >= 'A' THEN
995   3           IF BUFFER(0) <= 'Z' THEN
996   4             DO CASE BUFFER(0) AND 1FH;
997   4               ;
998   4               /* A */ CALL ENABLE_TEMPERATURE;
999   4               /* B */ CALL DISPLAY_TEMPERATURE_COUNT;
1000  4               /* C */ CALL DISPLAY_TEMPERATURE;
1001  4               /* D */ CALL COMPUTE_TEMPERATURE_BIAS;
1002  4               /* E */ CALL DISPLAY_BYTE (T_BIAS);
1003  4               /* F */ CALL ENABLE_CELL;
1004  4               /* G */ CALL DISPLAY_CELL_COUNT;
1005  4               /* H */ CALL NORMALIZE;
1006  4               /* I */ CALL DISPLAY_EMPTY_CELL_COUNT;
1007  4               /* J */ CALL DISPLAY_BYTE (M_LOWER);
1008  4               /* K */ CALL DISPLAY_BYTE (M_UPPER);
1009  4               /* L */ CALL DISPLAY_BYTE (BIAS);
1010  4               /* M */ ;
1011  4               /* N */ CALL STORE_CONFIGURATION;
1012  4               /* O */ CALL DISPLAY_BYTE (FLAGS);
1013  4               /* P */ CALL STORE_CALIBRATION;
1014  4               /* Q */ ;
1015  4               /* R */ ;
1016  4               /* S */ CALL RUN_CPU;
1017  4               /* T */ CALL TEST_DISPLAY;
1018  4               /* U */ ;
1019  4               /* V */ ;
1020  4               /* W */ POWER = 1;
1021  4               /* X */ ;
1022  4               /* Y */ ;
1023  4               /* Z */ OPEN = FALSE;
```

| | | |
|---|---|---|
| 1024 | 4 | END; |

/* Set power down to occur in 4.25 minutes except when power down has been requested. */

| | | |
|---|---|---|
| 1025 | 3 | IF POWER > 1 THEN POWER = 255; |

/* Prepare to receive the next command.
   CAUTION: The serial port may be active. Some routines have
        have reset N so that the next command can be received.
        If ENTER has been cleared the serial port needs no
        service here. */

| | | |
|---|---|---|
| 1027 | 3 | IF ENTER THEN |
| 1028 | 4 | DO; |
| 1029 | 4 | ENTER = FALSE; |
| 1030 | 4 | N = 0; |

/* Enable the serial receiver. */

| | | |
|---|---|---|
| 1031 | 4 | RCAP2H = 0FEH; |
| 1032 | 4 | RCAP2L = 0E1H; |
| 1033 | 4 | T2CON = 24H; |
| 1034 | 4 | SCON = 70H; |
| 1035 | 4 | ES = TRUE; |
| 1036 | 4 | END; |
| 1037 | 3 | END; |
| 1038 | 2 | ELSE |
| | | CALL IDLE; |
| 1039 | 2 | END; |

/* Disable the serial port. */

| | | |
|---|---|---|
| 1040 | 1 | ET1 = 0; |
| 1041 | 1 | TR1 = 0; |
| 1042 | 1 | ES = 0; |
| 1043 | 1 | TR2 = 0; |

/* Display an error if the cell is down. */

| | | |
|---|---|---|
| 1044 | 1 | IF FLOAT = 1 THEN |
| 1045 | 1 | IF TRIP = 0 THEN |
| 1046 | 1 | CALL TERMINATE (1); |

/* Read data from EEPROM. */

| | | |
|---|---|---|
| 1047 | 1 | FAIL = FALSE; |
| 1048 | 1 | T_BIAS     = RETRIEVE_BYTE (00H); |
| 1049 | 1 | EMPTY_CELL = RETRIEVE_WORD (03H); |
| 1050 | 1 | M_LOWER    = RETRIEVE_BYTE (09H); |
| 1051 | 1 | M_UPPER    = RETRIEVE_BYTE (0CH); |
| 1052 | 1 | BIAS       = RETRIEVE_BYTE (0FH); |
| 1053 | 1 | TL         = RETRIEVE_WORD (12H); |
| 1054 | 1 | FLAGS      = RETRIEVE_BYTE (18H); |
| 1055 | 1 | IF FAIL THEN CALL TERMINATE (2); |
| 1057 | 1 | GRAIN = RETRIEVE_BYTE (1BH); |
| 1058 | 1 | IF FAIL THEN GRAIN = 0; |
| 1060 | 1 | CALL RETRIEVE_CALIBRATION; |

/* The ID will be 0 if the there was an EEPROM read problem
   or the calibration checksum is bad. */

| | | |
|---|---|---|
| 1061 | 1 | IF CALIBRATION.ID = 0 THEN GRAIN = 0; |

```
                /* Check for special display requests. */

1063  1         IF GRAIN > 0 THEN
1064  2         DO;
1065  2           IF (UP = 0) AND (DOWN = 1) THEN
1066  3           DO;
                    /* Display calibration ID. */
1067  3             CALL DISPLAY_ID;
1068  3             POWER = 5;
1069  4             DO WHILE 1;
1070  4               CALL IDLE;
1071  4             END;
1072  3           END;
1073  2           ELSE IF (UP = 1) AND (DOWN = 0) THEN
1074  3           DO;
                    /* Display calibration bias. */
1075  3             CALL DISPLAY_CALIBRATION_BIAS;
1076  3             POWER = 5;
1077  4             DO WHILE 1;
1078  4               CALL IDLE;
1079  4             END;
1080  3           END;
1081  2         END;

/* To measure the empty cell the software sets the bit IE0 in register
                   TCON. This will generate an external interrupt 0. The interrupt
                   service routine will start the cell measurement. */

1082  1         RESULT = 0;
1083  1         CELL_PENDING = TRUE;
1084  1         EX0 = 1;
1085  1         IE0 = 1;
1086  2         DO WHILE CELL_PENDING;
1087  2           CALL IDLE;
1088  2         END;

/* Compare the empty cell reading to the stored reading. */

1089  1         IF RESULT > EMPTY_CELL THEN
1090  1             SCRATCH = RESULT - EMPTY_CELL;
1091  1         ELSE
                    SCRATCH = EMPTY_CELL - RESULT;
1092  1         IF SCRATCH > 300 THEN CALL TERMINATE (3);

/* Give the start pouring prompt. */

1094  1         PHASE = 1;
1095  1         CALL DISPLAY_GRAIN;

/* Initiate temperature measurment. The grain temperature is
                   measured at one second intervals. */

1096  1         N = 0;
1097  1         TEMP_CHECK = TRUE;
1098  1         TEMP_ERROR = FALSE;
1099  1         TEMP_LIMIT = FALSE;
```

```
1100  1       TEMP_VALID = FALSE;
1101  1       TEMP_ENABLED = TRUE;

/* The grain sample may now be poured into the cell or the UP and
                 DOWN buttons may be used to change the grain selection. */

1102  1       INC = FALSE;
1103  1       DEC = FALSE;
1104  1       LOOP = TRUE;
1105  2       DO WHILE LOOP;
1106  2         IF TEMP_ERROR THEN
1107  3           DO;
1108  3             TEMP_ENABLED = FALSE;
1109  3             CALL TERMINATE (4);
1110  3           END;
1111  2         ELSE IF INC THEN
1112  3           DO;
1113  4             DO WHILE INC;
1114  4               IF MULTI_GRAIN THEN
1115  4                 IF GRAIN = 12 THEN GRAIN = 0;
1117  4                 ELSE GRAIN = GRAIN + 1;
1118  4               ELSE
                        GRAIN = GRAIN + 1 AND 3;
1119  4               IF GRAIN = 0 THEN
1120  4                 INC = FALSE;
1121  4               ELSE
                        DO;
1122  5                 CALL RETRIEVE_CALIBRATION;
1123  5                 IF CALIBRATION.ID > 0 THEN INC = FALSE;
1125  5               END;
1126  4             END;
1127  3             CALL STORE_BYTE (GRAIN,1BH);
1128  3             CALL DISPLAY_GRAIN;
1129  3             POWER = 60;
1130  3           END;
1131  2         ELSE IF DEC THEN
1132  3           DO;
1133  4             DO WHILE DEC;
1134  4               IF MULTI_GRAIN THEN
1135  4                 IF GRAIN = 0 THEN GRAIN = 12;
1137  4                 ELSE GRAIN = GRAIN - 1;
1138  4               ELSE
                        GRAIN = GRAIN - 1 AND 3;
1139  4               IF GRAIN = 0 THEN
1140  4                 DEC = FALSE;
1141  4               ELSE
                        DO;
1142  5                 CALL RETRIEVE_CALIBRATION;
1143  5                 IF CALIBRATION.ID > 0 THEN DEC = FALSE;
1145  5               END;
1146  4             END;
1147  3             CALL STORE_BYTE (GRAIN,1BH);
1148  3             CALL DISPLAY_GRAIN;
1149  3             POWER = 60;
1150  3           END;
1151  2         IF FLOAT = 1 THEN LOOP = FALSE;
1153  2         IF LOOP THEN CALL IDLE;
```

| | | |
|---|---|---|
|1155|2|END;|

/* Enough grain has been poured into the cell to move it off the
   upper stop. Display the pour slowly prompt. */

| | | |
|---|---|---|
|1156|1|PHASE = 2;|
|1157|1|CALL DISPLAY_GRAIN;|

/* The full cell measurment will be taken when enough grain has
   been poured into the cell to cause the trip switch to close.
   The closure will generate an external interrupt and the service
   routine will start the full cell measurement. */

| | | |
|---|---|---|
|1158|1|CELL_PENDING = TRUE;|
|1159|1|IE0 = 0;|
|1160|1|EX0 = 1;|
|1161|2|DO WHILE CELL_PENDING;|
|1162|2|  CALL IDLE;|
|1163|2|END;|

/* At this point, RESULT = 1000 * ((empty cell count / full cell count) - 1).
   Now apply the normalization correction. */

| | | |
|---|---|---|
|1164|1|RESULT = CD_NORMAL;|
|1165|1|TEMP_COUNT = 0;|
|1166|1|PHASE = 3;|

/* If moisture prediction selected then use the selected calibration to
   compute the moisture. */

| | | |
|---|---|---|
|1167|1|IF GRAIN > 0 THEN CALL MOISTURE;|

/* Display chart data or moisture. */

| | | |
|---|---|---|
|1169|1|CALL DISPLAY_RESULT;|

/* Power down in 60 seconds. */

| | | |
|---|---|---|
|1170|1|POWER = 60;|

/* Loop until temperature measuremnent complete. */

| | | |
|---|---|---|
|1171|1|TIC = TIMER + 120;|
|1172|1|TOC = TIMER + 80;|
|1173|1|LOOP = TRUE;|
|1174|2|DO WHILE LOOP;|
|1175|2|  IF TIMER = TIC THEN|
|1176|3|    DO;|
|1177|3|      TIC = TIMER + 120;|

/* Display the result unless the temperature prediction is complete. */

| | | |
|---|---|---|
|1178|3|IF POWER_DOWN THEN BLANK = TRUE;|
|1180|3|ELSE IF TEMP_ENABLED THEN UPDATE = TRUE;|
|1182|3|ELSE LOOP = FALSE;|
|1183|3|END;|
|1184|2|ELSE IF TIMER = TOC THEN|
|1185|3|DO;|
|1186|3|  TOC = TIMER + 120;|

```
                    /* Blank the display. */
1187    3           BLANK = TRUE;
1188    3        END;
                    /* If the cell has been emptied then power down in 5 seconds. */
1189    2        IF FLOAT = 0 THEN
1190    2           IF POWER > 5 THEN POWER = 5;
                    /* Rest for a while. */
1192    2        IF LOOP THEN CALL IDLE;
1194    2     END;

/* If moisture prediction selected then apply the temperature compensation
                 to the apparent moisture. If the result exceeds the calibration limits
                 then flag an error. */

1195    1     IF GRAIN > 0 THEN
1196    2     DO;
                 /* Add the temperature correction to the apparent
                    moisture. */
1197    2        CALL TEMPERATURE_CORRECTION;
                 /* Check moisture limits. */
1198    2        MOISTURE_LIMIT = FALSE;
                 /* Upper limit. */
1199    2        IF RESULT < (CALIBRATION.MOISTURE(0) AND 1FFH) THEN
1200    2           MOISTURE_LIMIT = TRUE;
                 /* Lower limit. */
1201    2        IF RESULT > (CALIBRATION.MOISTURE(5) AND 1FFH) THEN
1202    2           MOISTURE_LIMIT = TRUE;
1203    2     END;

/* Display the result. */

1204    1     CALL DISPLAY_RESULT;
1205    1     PHASE = 4;

/* Loop until power down unless bias adjustment requested. */

1206    1     TIC = TIMER + 240;
1207    1     TOC = TIMER + 120;
1208    1     LOOP = TRUE;
1209    2     DO WHILE LOOP;
                 /* If the UP and DOWN buttons are both pressed then exit this loop. */
1210    2        IF (UP OR DOWN) = 0 THEN LOOP = FALSE;
1212    2        ELSE IF TIMER = TIC THEN
1213    3        DO;
1214    3           TIC = TIMER + 240;
1215    3           IF POWER_DOWN THEN BLANK = TRUE;
1217    3           ELSE CALL DISPLAY_RESULT;
1218    3        END;
1219    2        ELSE IF TIMER = TOC THEN
1220    3        DO;
1221    3           TOC = TIMER + 240;
1222    3           IF POWER_DOWN THEN BLANK = TRUE;
1224    3           ELSE IF GRAIN > 0 THEN
1225    4           DO;
1226    4              IF TEMP_LIMIT THEN CALL DISPLAY_ERROR (5);
1228    4              ELSE IF MOISTURE_LIMIT THEN CALL DISPLAY_ERROR (6);
1230    4           END;
```

```
1231   3              ELSE CALL DISPLAY_SAMPLE_TEMPERATURE;
1232   3              END;
                      /* If the cell has been emptied then power down in 5 seconds. */
1233   2              IF FLOAT = 0 THEN
1234   2                 IF POWER > 5 THEN POWER = 5;
                      /* Rest for a while. */
1236   2              IF LOOP THEN CALL IDLE;
1238   2              END;

/*** Now entering the bias adjustment zone! ***/

1239   1           PHASE = 5;

/* Power down in 60 seconds. */

1240   1           POWER = 60;

/* Display "—" until UP and DOWN buttons released. */

1241   1           CALL DISPLAY_SYMBOL (18);
1242   1           LOOP = TRUE;
1243   2           DO WHILE LOOP;
1244   2              IF UP AND DOWN THEN LOOP = FALSE;
1246   2              IF LOOP THEN CALL IDLE;
1248   2           END;

/* Display moisture or sample temperature. */

1249   1           IF GRAIN > 0 THEN CALL DISPLAY_RESULT;
1251   1           ELSE CALL DISPLAY_SAMPLE_TEMPERATURE;

/* Respond to UP and DOWN buttons. */

1252   1           INC = FALSE;
1253   1           DEC = FALSE;
1254   2           DO WHILE 1;
1255   2              IF INC THEN
1256   3              DO;
                      /* The UP button has been pressed. */
1257   3                 IF GRAIN > 0 THEN
1258   4                 DO;
                         /* Add .1 to the bias for this calibration. Clip the bias at +9.9. */
1259   4                    IF CALIBRATION.BIAS <> 063H THEN
1260   5                    DO;
1261   5                       CALIBRATION.BIAS = CALIBRATION.BIAS + 1;
1262   5                       CALL UPDATE_CALIBRATION_CKSM;
1263   5                       FAIL = FALSE;
1264   5                       CALL STORE_CALIBRATION_BIAS;
1265   5                       CALL STORE_CALIBRATION_CKSM;
1266   5                       IF FAIL THEN CALL DISPLAY_ERROR (2);
1268   5                       ELSE CALL DISPLAY_RESULT;
1269   5                    END;
1270   4                 END;
1271   3              ELSE
                      DO;
                      /* Add 1 to the temperature bias. Clip the temperature bias at +20.
                         NOTE: Temperature is in degrees Fahrenheit and T_BIAS is stored
``` in twos compliment notation to half degree resolution. */

```
1272   4        IF T_BIAS <> 028H THEN
1273   5          DO;
1274   5            T_BIAS = T_BIAS + 2;
1275   5            T_FINAL = T_FINAL + 2;
1276   5            FAIL = FALSE;
1277   5            CALL STORE_BYTE (T_BIAS,00H);
1278   5            IF FAIL THEN CALL DISPLAY_ERROR (2);
1280   5            ELSE CALL DISPLAY_SAMPLE_TEMPERATURE;
1281   5          END;
1282   4        END;
1283   3        INC = FALSE;
1284   3        POWER = 60;
1285   3      END;
1286   2      IF DEC THEN
1287   3        DO;
                 /* The DOWN button has been pressed. */
1288   3        IF GRAIN > 0 THEN
1289   4          DO;
                   /* Subtract .1 from the bias for this calibration. Clip the
                      bias at -9.9. */
1290   4          IF CALIBRATION.BIAS <> 09DH THEN
1291   5            DO;
1292   5              CALIBRATION.BIAS = CALIBRATION.BIAS - 1;
1293   5              CALL UPDATE_CALIBRATION_CKSM;
1294   5              FAIL = FALSE;
1295   5              CALL STORE_CALIBRATION_BIAS;
1296   5              CALL STORE_CALIBRATION_CKSM;
1297   5              IF FAIL THEN CALL DISPLAY_ERROR (2);
1299   5              ELSE CALL DISPLAY_RESULT;
1300   5            END;
1301   4          END;
1302   3        ELSE
                 DO;
                   /* Subtract 1 from the temperature bias. Clip the temperature
                      bias at -20.
                      NOTE: Temperature is in degrees Fahrenheit and T_BIAS is stored
                            in twos compliment notation to half degree resolution. */
1303   4        IF T_BIAS <> 0D8H THEN
1304   5          DO;
1305   5            T_BIAS = T_BIAS - 2;
1306   5            T_FINAL = T_FINAL - 2;
1307   5            FAIL = FALSE;
1308   5            CALL STORE_BYTE (T_BIAS,00H);
1309   5            IF FAIL THEN CALL DISPLAY_ERROR (2);
1311   5            ELSE CALL DISPLAY_SAMPLE_TEMPERATURE;
1312   5          END;
1313   4        END;
1314   3        DEC = FALSE;
1315   3        POWER = 60;
1316   3      END;
               /* If the cell has been emptied then power down in 5 seconds. */
1317   2      IF FLOAT = 0 THEN
1318   2        IF POWER > 5 THEN POWER = 5;
               /* Rest for a while. */
1320   2      CALL IDLE;
1321   2    END;
```

```
1322    1       END;
```

WARNINGS:
    5 IS THE HIGHEST USED INTERRUPT

MODULE INFORMATION:            (STATIC+OVERLAYABLE)
    CODE SIZE               = 1662H      5730D
    CONSTANT SIZE           = 0145H       325D
    DIRECT VARIABLE SIZE    =   36H+10H   54D+ 16D
    INDIRECT VARIABLE SIZE  =   22H+00H   34D+  0D
    BIT SIZE                =   15H+00H   21D+  0D
    BIT-ADDRESSABLE SIZE    =   00H+00H    0D+  0D
    AUXILIARY VARIABLE SIZE = 0000H        0D
    MAXIMUM STACK SIZE      = 0029H       41D
    REGISTER-BANK(S) USED:     0 1 2
    1935 LINES READ
    0 PROGRAM ERROR(S)
END OF PL/M-51 COMPILATION

```
LOC  OBJ          LINE     SOURCE

1      $ TITLE(GMT II - DENNIS E. GRIM)
                    2      $ DEBUG
                    3      ;
                    4      ;***********************************************************************
                    5      ;*                                                                     *
                    6      ;*                                                                     *
                    7      ;*            COPYRIGHT (c) 1988                                       *
                    8      ;*            DICKEY-john Corporation                                  *
                    9      ;*            Auburn, Illinois                                         *
                   10      ;*                                                                     *
                   11      ;*                                                                     *
                   12      ;***********************************************************************
                   13      ;
                   14                    NAME    GMT_2
                   15      ;
                   16      ?GMT_2?BI     SEGMENT BIT
                   17      ?GMT_2?DA     SEGMENT DATA
                   18      ?GMT_2?PR     SEGMENT CODE
                   19      ;
                   20      ;***********************************************************************
                   21      ;
                   22      ; PROVIDE THE AC DRIVE FOR THE LCD.
                   23      ;
                   24      ; THE ENABLED DISPLAY SEGMENTS ARE ALTERNATELY DRIVEN TO 5 VDC
                   25      ; THEN 0 VDC WHILE THE DISABLED SEGMENTS AND THE BACKPLANE ARE
                   26      ; DRIVEN TO THE SAME VOLTAGES 180 DEGREES OUT OF PHASE.  THE
                   27      ; SEGMENT DRIVERS ARE UPDATED AT 8.3 MILLISECOND INTERVALS.
                   28      ;
0083               29      BP        EQU   083H    ;LCD BACKPLANE BIT ADDRESS
0040               30      DP        EQU   040H    ;LCD DECIMAL POINT DATA
0048               31      MASK_0    EQU   048H    ;PORT 0 LCD BITS
```

```
OOFF              32    MASK_1      EQU    OFFH       ;PORT 1 LCD BITS
OOFF              33    MASK_2      EQU    OFFH       ;PORT 2 LCD BITS
OODA              34    MASK_3      EQU    ODAH       ;PORT 3 LCD BITS
                  35    ;
                  36                EXTRN  BIT(UPDATE,BLANK,POINT)
                  37                EXTRN  DATA(DISPLAY)
                  38    ;
                  39                PUBLIC LCD_DRIVE
                  40                RSEG   ?GNT_2?PR
                  41    ;
0000 200010  F    42    LCD_DRIVE:  JB     UPDATE,LCD_1   ;JUMP TO UPDATE DISPLAY
0003 20000D  F    43                JB     BLANK,LCD_1    ;JUMP TO BLANK DISPLAY
                  44    ;
0006 638048       45    LCD_2:      XRL    P0,#MASK_0     ;FLIP ALL SEGMENTS AND
0009 6390FF       46                XRL    P1,#MASK_1     ;THE BACKPLANE
000C 63A0FF       47                XRL    P2,#MASK_2
000F 63B0DA       48                XRL    P3,#MASK_3
0012 22           49                RET
                  50    ;
0013 3083F0       51    LCD_1:      JNB    BP,LCD_2       ;SYNCHRONIZE CHANGE WITH BACKPLANE
0016 5380B7       52                ANL    P0,#NOT MASK_0 ;CLEAR OLD SEGMENT DATA
0019 539000       53                ANL    P1,#NOT MASK_1
001C 53A000       54                ANL    P2,#NOT MASK_2
001F 53B025       55                ANL    P3,#NOT MASK_3
0022 100014  F    56                JBC    BLANK,LCD_3    ;JUMP FOR BLANK DISPLAY
0025 300003  F    57                JNB    POINT,LCD_4    ;OUTPUT NEW SEGMENT DATA
0028 438040       58                ORL    P0,#DP
002B E500    F    59    LCD_4:      MOV    A,DISPLAY+0
002D 4290         60                ORL    P1,A
002F E500    F    61                MOV    A,DISPLAY+1
0031 42A0         62                ORL    P2,A
0033 E500    F    63                MOV    A,DISPLAY+2
0035 42B0         64                ORL    P3,A
0037 C200    F    65                CLR    UPDATE         ;UPDATE COMPLETE
0039 22           66    LCD_3:      RET
                  67    ;
                  68    ;##################################################################
                  69    ;
                  70    ; Read data from the X2402 EEPROM.
                  71    ;
                  72    ; R0 - RAM pointer (destination address)
                  73    ; R1 - byte count
                  74    ; R2 - busy timer
                  75    ; R3 - retry count
                  76    ; R6 - shift register
                  77    ; R7 - bit count
                  78    ;
0084              79    SDA         EQU    084H       ;X2402 serial data line
0086              80    SCL         EQU    086H       ;x2402 serail clock line
                  81    ;
                  82                EXTRN  BIT(ACK,FAIL)
                  83    ;
                  84                PUBLIC ?READ?BYTE,READ
                  85    ;
                  86                RSEG   ?GNT_2?DA
                  87    ;
                  88    ?READ?BYTE:
```

```
0000                    89   RD_SRC:      DS      1          ;source (EEPROM) address
0001                    90   RD_DST:      DS      1          ;destination (RAM) address
0002                    91   COUNT:       DS      1          ;number of bytes to read
                        92   ;
                        93                RSEG    ?GMT_2?PR
                        94   ;
                        95   READ:
                        96   ;
                        97   ; try up to three times to read data from the X2402
                        98   ;
003A 7B03               99                MOV     R3,#3
                       100   ;
                       101   ; X2402 busy check
                       102   ;
                       103   R_5:
003C 120000      F     104                LCALL   BUSY
003F 200055      F     105                JB      FAIL,R_1   ;jump if X2402 will not respond
                       106   ;
                       107   ; initialization
                       108   ;
0042 A800        F     109                MOV     R0,RD_DST  ;RAM pointer
0044 A900        F     110                MOV     R1,COUNT   ;byte count
                       111   ;
                       112   ; start condition
                       113   ;
0046 C286              114                CLR     SCL
0048 D284              115                SETB    SDA
004A D286              116                SETB    SCL
004C A4                117                MUL     AB         ;start condition setup
004D C284              118                CLR     SDA        ;start condition
004F A4                119                MUL     AB         ;start condition hold
0050 C286              120                CLR     SCL        ;serial clock low
                       121   ;
                       122   ; slave address (dummy write)
                       123   ;
0052 7EA0              124                MOV     R6,#0A0H
0054 120000      F     125                LCALL   OUT
0057 20002C      F     126                JB      ACK,R_2    ;jump if no ACK
                       127   ;
                       128   ; word address
                       129   ;
005A AE00        F     130                MOV     R6,RD_SRC
005C 120000      F     131                LCALL   OUT
005F 200024      F     132                JB      ACK,R_2    ;jump if no ACK
                       133   ;
                       134   ; start condition (restart)
                       135   ;
0062 A4                136                MUL     AB         ;clock low period
0063 D286              137                SETB    SCL
0065 A4                138                MUL     AB         ;start condition setup
0066 C284              139                CLR     SDA        ;start condition
0068 A4                140                MUL     AB         ;start condition hold
0069 C286              141                CLR     SCL        ;serial clock low
                       142   ;
                       143   ; slave address (read)
                       144   ;
006B 7EA1              145                MOV     R6,#0A1H   ;slave address for read
006D 120000      F     146                LCALL   OUT
```

```
0070 200013    F    147              JB       ACK,R_2      ;jump if no ACK
                    148      ;
                    149      ; data word
                    150      ;
                    151      R_6:
0073 7F08            152              MOV      R7,#8        ;bit count
                    153      R_3:
0075 A4              154              MUL      AB           ;clock low period
0076 00              155              NOP
0077 D286            156              SETB     SCL          ;serial clock high
0079 A284            157              MOV      C,SDA        ;serial data
007B EE              158              MOV      A,R6         ;shift bit pattern
007C 33              159              RLC      A
007D FE              160              MOV      R6,A
007E C286            161              CLR      SCL          ;serial clock low
0080 DFF3            162              DJNZ     R7,R_3       ;go back for next bit
0082 EE              163              MOV      A,R6         ;save data word
0083 F6              164              MOV      @R0,A
                    165      ;
                    166      ; acknowledge the data word only if reading will continue
                    167      ;
0084 D912            168              DJNZ     R1,R_4       ;jump for acknowledge
                    169      ;
                    170      ; stop condition
                    171      ;
                    172      R_2:
0086 C284            173              CLR      SDA
0088 D286            174              SETB     SCL
008A A4              175              MUL      AB           ;stop condition setup
008B D284            176              SETB     SDA          ;stop condition
008D A4              177              MUL      AB           ;stop condition hold
008E C286            178              CLR      SCL          ;decimal point = backplane
                    179      ;
                    180      ; try again if needed
                    181      ;
0090 300004    F    182              JNB      ACK,R_1      ;jump if all ACKs valid
0093 DBA7            183              DJNZ     R3,R_5
0095 D200      F    184              SETB     FAIL
                    185      ;
                    186      ; done
                    187      ;
                    188      R_1:
0097 22              189              RET
                    190      ;
                    191      ; acknowledge the data word
                    192      ;
                    193      R_4:
0098 C284            194              CLR      SDA          ;ACK bit - serial data low
009A D286            195              SETB     SCL          ;serial clock high
009C A4              196              MUL      AB           ;clock high period
009D C286            197              CLR      SCL          ;serial clock low
009F D284            198              SETB     SDA          ;release SDA line - serial data high
00A1 08              199              INC      R0           ;increment destination address
00A2 80CF            200              SJMP     R_6          ;go back for next data word
                    201      ;
                    202      ;################################################################
                    203      ;
```

```
                    204   ; Write data to the X2402 EEPROM.
                    205   ;
                    206   ; R0 - RAM pointer (source address)
                    207   ; R1 - byte count
                    208   ; R2 - busy timer
                    209   ; R3 - retry count
                    210   ; R6 - shift register
                    211   ; R7 - bit count
                    212   ;
                    213           PUBLIC  ?WRITE?BIT,?WRITE?BYTE,WRITE
                    214   ;
                    215           RSEG    ?GMT_2?BI
                    216   ;
                    217   ?WRITE?BIT:
0000                218   PAGE_WR:    DBIT    1              ;page write flag
                    219   ;
                    220           RSEG    ?GMT_2?DA
                    221   ;
                    222   ?WRITE?BYTE:
0003                223   WR_SRC:     DS      1              ;source (RAM) address
0004                224   WR_DST:     DS      1              ;destination (EEPROM) address
                    225   ;
                    226           RSEG    ?GMT_2?PR
                    227   ;
                    228   WRITE:
                    229   ;
                    230   ; try up to three times to write data to the X2402
                    231   ;
00A4 7B03           232           MOV     R3,#3
                    233   ;
                    234   ; X2402 busy check
                    235   ;
                    236   W_5:
00A6 120000  F      237           LCALL   BUSY
00A9 200042  F      238           JB      FAIL,W_1       ;jump if X2402 will not respond
                    239   ;
                    240   ; initialization
                    241   ;
00AC A800    F      242           MOV     R0,WR_SRC      ;RAM pointer
00AE 7901           243           MOV     R1,#1          ;byte write
00B0 300002  F      244           JNB     PAGE_WR,W_2
00B3 7908           245           MOV     R1,#8          ;page write
                    246   ;
                    247   ; start condition
                    248   ;
                    249   W_2:
00B5 C286           250           CLR     SCL
00B7 D284           251           SETB    SDA
00B9 D286           252           SETB    SCL
00BB A4             253           MUL     AB             ;start condition setup
00BC C284           254           CLR     SDA            ;start condition
00BE A4             255           MUL     AB             ;start condition hold
00BF C286           256           CLR     SCL            ;serial clock low
                    257   ;
                    258   ; slave address (write)
                    259   ;
00C1 7EA0           260           MOV     R6,#0A0H
```

```
00C3 120000  F   261                LCALL  OUT
00C6 200013  F   262                JB     ACK,W_3         ;jump if no ACK
                 263     ;
                 264     ; word address
                 265     ;
00C9 AE00    F   266                MOV    R6,WR_DST
00CB 120000  F   267                LCALL  OUT
00CE 20000B  F   268                JB     ACK,W_3         ;jump if no ACK
                 269     ;
                 270     ; data word
                 271     ;
                 272     W_4:
00D1 E6          273                MOV    A,@R0
00D2 FE          274                MOV    R6,A
00D3 120000  F   275                LCALL  OUT
00D6 200003  F   276                JB     ACK,W_3         ;jump if no ACK
                 277     ;
                 278     ; go back for next byte (page write only)
                 279     ;
00D9 08          280                INC    R0
00DA D9F5        281                DJNZ   R1,W_4
                 282     ;
                 283     ; stop condition
                 284     ;
                 285     W_3:
00DC A4          286                MUL    AB              ;clock low period
00DD C284        287                CLR    SDA
00DF D286        288                SETB   SCL
00E1 A4          289                MUL    AB              ;stop condition setup
00E2 D284        290                SETB   SDA             ;stop condition
00E4 A4          291                MUL    AB              ;stop condition hold
00E5 C286        292                CLR    SCL             ;decimal point = backplane
                 293     ;
                 294     ; try again if needed
                 295     ;
00E7 300004  F   296                JNB    ACK,W_1         ;jump if all ACKs valid
00EA DBBA        297                DJNZ   R3,W_5
00EC D200    F   298                SETB   FAIL
                 299     ;
                 300     ; done
                 301     ;
                 302     W_1:
00EE 22          303                RET
                 304     ;
                 305     ;################################################################
                 306     ;
                 307     ; Used by READ and WRITE to wait while the X2402 is busy.
                 308     ;
                 309     ; R2 - busy timer
                 310     ; R6 - shift register
                 311     ;
                 312     BUSY:
00EF 7A00        313                MOV    R2,#0           ;busy wait timer
                 314     ;
                 315     ; start condition
                 316     ;
                 317     B_2:
```

```
00F1 C286         318                 CLR    SCL
00F3 D284         319                 SETB   SDA
00F5 D286         320                 SETB   SCL
00F7 A4           321                 MUL    AB              ;start condition setup
00F8 C284         322                 CLR    SDA             ;start condition
00FA A4           323                 MUL    AB              ;start condition hold
00FB C286         324                 CLR    SCL             ;serial clock low
                  325         ;
                  326         ; slave address (write)
                  327         ;
00FD 7EA0         328                 MOV    R6,#0A0H
00FF 120000   F   329                 LCALL  OUT
                  330         ;
                  331         ; acknowledge polling (ACK invalid if X2402 is busy)
                  332         ;
0102 300004   F   333                 JNB    ACK,B_1         ;jump if ACK valid
0105 DAEA         334                 DJNZ   R2,B_2          ;jump if still waiting
0107 D200     F   335                 SETB   FAIL            ;note EEPROM failure
                  336         B_1:
0109 22           337                 RET                    ;all done here
                  338         ;
                  339         ;###############################################################
                  340         ;
                  341         ; Used by READ and Write to send a byte to the X2402.
                  342         ;
                  343         ; R6 - shift register
                  344         ; R7 - bit count
                  345         ;
                  346         OUT:
010A 7F08         347                 MOV    R7,#8           ;bit count
                  348         ;
                  349         ; shift byte out to X2402
                  350         ;
                  351         OUT_1:
010C EE           352                 MOV    A,R6            ;shift bit pattern
010D 33           353                 RLC    A
010E FE           354                 MOV    R6,A
010F 9284         355                 MOV    SDA,C           ;serial data
0111 D286         356                 SETB   SCL             ;serial clock high
0113 A4           357                 MUL    AB              ;clock high period
0114 C286         358                 CLR    SCL             ;serial clock low
0116 DFF4         359                 DJNZ   R7,OUT_1        ;go back for next bit
                  360         ;
                  361         ; acknowledge from X2402
                  362         ;
0118 D284         363                 SETB   SDA             ;release SDA line
011A A4           364                 MUL    AB              ;clock low period
011B D286         365                 SETB   SCL             ;serial clock high
011D A284         366                 MOV    C,SDA           ;note ACK
011F 9200     F   367                 MOV    ACK,C
0121 00           368                 NOP                    ;clock high period
0122 C286         369                 CLR    SCL             ;serial clock low
                  370         ;
                  371         ; done
                  372         ;
0124 22           373                 RET
                  374         ;
                  375         ;###############################################################
```

```
376  ;
377  ; CHART DATA CALCULATIONS
378  ;
379  ; CD_RATIO = ((EMPTY CELL COUNT / FULL CELL COUNT) - 1) * 1000
380  ; NOTE: VALID ONLY WHEN FULL CELL COUNT > EMPTY CELL COUNT/2
381  ;
382  ; CD_NORMAL = ( CD_RATIO / M_UPPER) + BIAS
383  ; IF CD_NORMAL < TL THEN   (NOTE: TL = LOWER NORMALIZATION TARGET VALUE)
384  ;   CD_NORMAL = CD_RATIO / M_LOWER
385  ;.
386  ; CD = (CD_NORMAL + 500) / 10
387  ; NOTE: THIS CALCULATION IS PERFORMED IN THE DISPLAY ROUTINE.  THE
388  ;       FORMULA IS GIVEN HERE ONLY FOR REFERENCE.  THE DIVIDE BY TEN
389  ;       IS DONE BY PLACEMENT OF THE DECIMAL POINT ON THE DISPLAY.
390  ;
391  ; NOTE: CD IS USED WITH CONVERSION CHARTS WHEN THERE IS NO INTERNALLY
392  ;       STORED CALIBRATION FOR THE PRODUCT BEING MEASURED OR IS USED
393  ;       FOR CALIBRATION DEVELOPMENT.  CD_NORMAL IS USED AS INPUT TO
394  ;       THE INTERNALLY STORED CALIBRATIONS.
395  ;
396  ;##############################################################
397  ;
398  ; CD_RATIO = ((EMPTY CELL COUNT / FULL CELL COUNT) - 1) * 1000
399  ;
400  ; USE THE SAME REGISTER BANK AS THE CALLING ROUTINE
401  ;
402              EXTRN   DATA(RESULT)
403  ;
404              PUBLIC  CD_RATIO
405              RSEG    ?GMT_2?PR
406  ;
407  CD_RATIO:
408  ;
409  ; EMPTY CELL COUNT / FULL CELL COUNT
410  ;
0125 A800   F  411          MOV     R0,RESULT       ;LOAD DIVIDEND (EMPTY CELL)
0127 A900   F  412          MOV     R1,RESULT+1
0129 AA8D      413          MOV     R2,TH1          ;LOAD DIVISOR (FULL CELL)
012B AB8B      414          MOV     R3,TL1
012D 7C00      415          MOV     R4,#0           ;CLEAR QUOTIENT
012F 7D00      416          MOV     R5,#0
0131 7E0D      417          MOV     R6,#13          ;SET QUOTIENT BIT COUNT
               418  ;
0133 C3        419  CDR2:   CLR     C               ;DIFFERENCE = DIVIDEND - DIVISOR
0134 E9        420          MOV     A,R1
0135 9B        421          SUBB    A,R3
0136 FF        422          MOV     R7,A
0137 E8        423          MOV     A,R0
0138 9A        424          SUBB    A,R2
               425  ;
0139 4003      426          JC      CDR1            ;JUMP IF UNDERFLOW
               427  ;
013B F8        428          MOV     R0,A            ;DIVIDEND = DIFFERENCE
013C EF        429          MOV     A,R7
013D F9        430          MOV     R1,A
               431  ;
013E B3        432  CDR1:   CPL     C               ;SHIFT BIT INTO QUOTIENT
013F ED        433          MOV     A,R5
```

```
0140 33        434              RLC    A
0141 FD        435              MOV    R5,A
0142 EC        436              MOV    A,R4
0143 33        437              RLC    A
0144 FC        438              MOV    R4,A
               439       ;
0145 E9        440              MOV    A,R1      ;SHIFT DIVIDEND LEFT
0146 33        441              RLC    A
0147 F9        442              MOV    R1,A
0148 E8        443              MOV    A,R0
0149 33        444              RLC    A
014A F8        445              MOV    R0,A
               446       ;
014B DEE6      447              DJNZ   R6,CDR2   ;DEC BIT COUNT
               448       ;
014D EC        449              MOV    A,R4      ;IF QUOTIENT < 1 THEN
014E 5410      450              ANL    A,#10H
0150 7004      451              JNZ    CDR3
0152 7C00      452              MOV    R4,#0     ;QUOTIENT = 0.0
0154 7D00      453              MOV    R5,#0
               454       ;
               455       ; QUOTIENT - 1
               456       ;
0156 EC        457       CDR3:  MOV    A,R4
0157 540F      458              ANL    A,#0FH
0159 FC        459              MOV    R4,A
               460       ;
               461       ; DIFFERENCE * 1000
               462       ; NOTE: 12 BITS * 7 BITS YIELDS 19 BITS
               463       ;
015A ED        464              MOV    A,R5
015B 75F07D    465              MOV    B,#125    ;NOTE: 125 * 2^3 = 1000
015E A4        466              MUL    AB
015F AFF0      467              MOV    R7,B      ;DISCARD LOWER 8 BITS
0161 EC        468              MOV    A,R4
0162 75F07D    469              MOV    B,#125
0165 A4        470              MUL    AB
0166 2F        471              ADD    A,R7
0167 FF        472              MOV    R7,A
0168 E4        473              CLR    A
0169 35F0      474              ADDC   A,B
016B FE        475              MOV    R6,A
               476       ;
               477       ; ROUND TO UNITS
               478       ;
016C EF        479              MOV    A,R7
016D 2401      480              ADD    A,#1
016F FF        481              MOV    R7,A
0170 EE        482              MOV    A,R6
0171 3400      483              ADDC   A,#0
0173 13        484              RRC    A
0174 FE        485              MOV    R6,A
0175 EF        486              MOV    A,R7
0176 13        487              RRC    A
0177 FF        488              MOV    R7,A
               489       ;
               490       ; FINISHED
```

```
                491   ;
0178 22         492           RET
                493   ;
                494   ;###############################################################
                495   ;
                496   ; CD_NORMAL = ( CD_RATIO / M_UPPER) + BIAS
                497   ;   OR
                498   ; CD_NORMAL = CD_RATIO / M_LOWER
                499   ;
                500           EXTRN   DATA(M_UPPER,BIAS,TL,M_LOWER)
                501   ;
                502           PUBLIC  CD_NORMAL
                503           RSEG    ?GMT_2?PR
                504   ;
                505   CD_NORMAL:
                506   ;
                507   ; CD_NORMAL = ( CD_RATIO / M_UPPER) + BIAS
                508   ;
0179 7800       509           MOV     R0,#0           ;LOAD DIVIDEND
017B A900    F  510           MOV     R1,RESULT
017D AA00    F  511           MOV     R2,RESULT+1
017F 7D12       512           MOV     R5,#18          ;SET QUOTIENT BIT COUNT
0181 7E00       513           MOV     R6,#0           ;CLEAR QUOTIENT
0183 7F00       514           MOV     R7,#0
                515   ;
0185 C3         516   CDN2:   CLR     C               ;DIFFERENCE = DIVIDEND - DIVISOR
0186 E9         517           MOV     A,R1
0187 9500    F  518           SUBB    A,M_UPPER
0189 FB         519           MOV     R3,A
018A E8         520           MOV     A,R0
018B 9400       521           SUBB    A,#0
                522   ;
018D 4003       523           JC      CDN1            ;JUMP IF UNDERFLOW
                524   ;
018F F8         525           MOV     R0,A            ;DIVIDEND = DIFFERENCE
0190 EB         526           MOV     A,R3
0191 F9         527           MOV     R1,A
                528   ;
0192 B3         529   CDN1:   CPL     C               ;SHIFT BIT INTO QUOTIENT
0193 EF         530           MOV     A,R7
0194 33         531           RLC     A
0195 FF         532           MOV     R7,A
0196 EE         533           MOV     A,R6
0197 33         534           RLC     A
0198 FE         535           MOV     R6,A
                536   ;
0199 EA         537           MOV     A,R2            ;SHIFT DIVIDEND LEFT
019A 33         538           RLC     A
019B FA         539           MOV     R2,A
019C E9         540           MOV     A,R1
019D 33         541           RLC     A
019E F9         542           MOV     R1,A
019F E8         543           MOV     A,R0
01A0 33         544           RLC     A
01A1 F8         545           MOV     R0,A
                546   ;
01A2 DDE1       547           DJNZ    R5,CDN2         ;DEC BIT COUNT
                548   ;
```

```
                549    ; ROUND TO UNITS
                550    ;
01A4 EF         551            MOV     A,R7
01A5 2402       552            ADD     A,#2
01A7 FF         553            MOV     R7,A
01A8 EE         554            MOV     A,R6
01A9 3400       555            ADDC    A,#0
01AB 13         556            RRC     A
01AC FE         557            MOV     R6,A
01AD EF         558            MOV     A,R7
01AE 13         559            RRC     A
01AF FF         560            MOV     R7,A
01B0 C3         561            CLR     C
01B1 EE         562            MOV     A,R6
01B2 13         563            RRC     A
01B3 FE         564            MOV     R6,A
01B4 EF         565            MOV     A,R7
01B5 13         566            RRC     A
01B6 FF         567            MOV     R7,A
                568    ;
                569    ; ROUNDED QUOTIENT + B
                570    ;
01B7 E500    F  571            MOV     A,BIAS
01B9 A2E7       572            MOV     C,ACC.7
01BB 92D5       573            MOV     F0,C            ;NOTE POLARITY OF BIAS
01BD 2F         574            ADD     A,R7
01BE FF         575            MOV     R7,A
01BF E4         576            CLR     A               ;FOR POSITIVE BIAS
01C0 30D501     577            JNB     F0,CDN3
01C3 F4         578            CPL     A               ;FOR NEGATIVE BIAS
01C4 3E         579    CDN3:   ADDC    A,R6
01C5 FE         580            MOV     R6,A
                581    ;
                582    ; CLIP SUM AT 0 (A NEGATIVE BIAS MIGHT CAUSE A NEGATIVE SUM)
                583    ;
01C6 30E704     584            JNB     ACC.7,CDN4      ;JUMP IF SUM IS POSITIVE
01C9 7E00       585            MOV     R6,#0           ;SUM = 0
01CB 7F00       586            MOV     R7,#0
                587    ;
                588    ; COMPARE SUM TO TL
                589    ;
01CD C3         590    CDN4:   CLR     C               ;SUM - TL
01CE EF         591            MOV     A,R7
01CF 9500    F  592            SUBB    A,TL+1
01D1 EE         593            MOV     A,R6
01D2 9500    F  594            SUBB    A,TL
                595    ;
01D4 503E       596            JNC     CDN5            ;JUMP IF SUM >= TL
                597    ;
                598    ; CD_NORMAL = CD_RATIO / M_LOWER
                599    ;
01D6 7800       600            MOV     R0,#0           ;LOAD DIVIDEND
01D8 A900    F  601            MOV     R1,RESULT
01DA AA00    F  602            MOV     R2,RESULT+1
01DC 7D12       603            MOV     R5,#18          ;SET QUOTIENT BIT COUNT
01DE 7E00       604            MOV     R6,#0           ;CLEAR QUOTIENT
01E0 7F00       605            MOV     R7,#0
```

| | 606 | ; | | | |
|---|---|---|---|---|---|
| 01E2 C3 | 607 | CDN7: | CLR | C | ;DIFFERENCE = DIVIDEND - DIVISOR |
| 01E3 E9 | 608 | | MOV | A,R1 | |
| 01E4 9500 F | 609 | | SUBB | A,M_LOWER | |
| 01E6 FB | 610 | | MOV | R3,A | |
| 01E7 E8 | 611 | | MOV | A,R0 | |
| 01E8 9400 | 612 | | SUBB | A,#0 | |
| | 613 | ; | | | |
| 01EA 4003 | 614 | | JC | CDN6 | ;JUMP IF UNDERFLOW |
| | 615 | ; | | | |
| 01EC F8 | 616 | | MOV | R0,A | ;DIVIDEND = DIFFERENCE |
| 01ED EB | 617 | | MOV | A,R3 | |
| 01EE F9 | 618 | | MOV | R1,A | |
| | 619 | ; | | | |
| 01EF B3 | 620 | CDN6: | CPL | C | ;SHIFT BIT INTO QUOTIENT |
| 01F0 EF | 621 | | MOV | A,R7 | |
| 01F1 33 | 622 | | RLC | A | |
| 01F2 FF | 623 | | MOV | R7,A | |
| 01F3 EE | 624 | | MOV | A,R6 | |
| 01F4 33 | 625 | | RLC | A | |
| 01F5 FE | 626 | | MOV | R6,A | |
| | 627 | ; | | | |
| 01F6 EA | 628 | | MOV | A,R2 | ;SHIFT DIVIDEND LEFT |
| 01F7 33 | 629 | | RLC | A | |
| 01F8 FA | 630 | | MOV | R2,A | |
| 01F9 E9 | 631 | | MOV | A,R1 | |
| 01FA 33 | 632 | | RLC | A | |
| 01FB F9 | 633 | | MOV | R1,A | |
| 01FC E8 | 634 | | MOV | A,R0 | |
| 01FD 33 | 635 | | RLC | A | |
| 01FE F8 | 636 | | MOV | R0,A | |
| | 637 | ; | | | |
| 01FF DDE1 | 638 | | DJNZ | R5,CDN7 | ;DEC BIT COUNT |
| | 639 | ; | | | |
| | 640 | ; ROUND TO UNITS | | | |
| | 641 | ; | | | |
| 0201 EF | 642 | | MOV | A,R7 | |
| 0202 2402 | 643 | | ADD | A,#2 | |
| 0204 FF | 644 | | MOV | R7,A | |
| 0205 EE | 645 | | MOV | A,R6 | |
| 0206 3400 | 646 | | ADDC | A,#0 | |
| 0208 13 | 647 | | RRC | A | |
| 0209 FE | 648 | | MOV | R6,A | |
| 020A EF | 649 | | MOV | A,R7 | |
| 020B 13 | 650 | | RRC | A | |
| 020C FF | 651 | | MOV | R7,A | |
| 020D C3 | 652 | | CLR | C | |
| 020E EE | 653 | | MOV | A,R6 | |
| 020F 13 | 654 | | RRC | A | |
| 0210 FE | 655 | | MOV | R6,A | |
| 0211 EF | 656 | | MOV | A,R7 | |
| 0212 13 | 657 | | RRC | A | |
| 0213 FF | 658 | | MOV | R7,A | |
| | 659 | ; | | | |
| | 660 | ;.FINISHED | | | |
| | 661 | ; | | | |
| 0214 22 | 662 | CDN5: | RET | | |
| | 663 | ; | | | |

```
                        664   ;####################################################################
                        665   ;
                        666   ; COMPUTE THE NORMALIZATION SLOPE.
                        667   ;
                        668   ; M_UPPER = (CH - CL) / (TH - TL)
                        669   ; OR
                        670   ; M_LOWER = CL / TL
                        671   ; (NOTE: THE SAME ROUTINE IS USED FOR BOTH)
                        672   ;
                        673                   EXTRN   DATA(SCRATCH)
                        674   ;
                        675                   PUBLIC  SLOPE
                        676                   RSEG    ?GMT_2?PR
                        677   ;
                        678   SLOPE:
0215 A800     F         679           MOV     R0,RESULT       ;LOAD DIVIDEND (CH - CL)
0217 A900     F         680           MOV     R1,RESULT+1     ; OR CL
0219 AA00     F         681           MOV     R2,SCRATCH      ;LOAD DIVISOR (TH - TL)
021B AB00     F         682           MOV     R3,SCRATCH+1    ; OR TL
021D 7C09               683           MOV     R4,#9           ;SET QUOTIENT BIT COUNT
021F 7E00               684           MOV     R6,#0           ;CLEAR QUOTIENT
0221 7F00               685           MOV     R7,#0
                        686   ;
0223 C3                 687   S2:     CLR     C               ;DIFFERENCE = DIVIDEND - DIVISOR
0224 E9                 688           MOV     A,R1
0225 9B                 689           SUBB    A,R3
0226 FD                 690           MOV     R5,A
0227 E8                 691           MOV     A,R0
0228 9A                 692           SUBB    A,R2
                        693   ;
0229 4003               694           JC      S1              ;JUMP IF UNDERFLOW
                        695   ;
022B F8                 696           MOV     R0,A            ;DIVIDEND = DIFFERENCE
022C ED                 697           MOV     A,R5
022D F9                 698           MOV     R1,A
                        699   ;
022E B3                 700   S1:     CPL     C               ;SHIFT BIT INTO QUOTIENT
022F EF                 701           MOV     A,R7
0230 33                 702           RLC     A
0231 FF                 703           MOV     R7,A
0232 EE                 704           MOV     A,R6
0233 33                 705           RLC     A
0234 FE                 706           MOV     R6,A
                        707   ;
0235 E9                 708           MOV     A,R1            ;SHIFT DIVIDEND LEFT
0236 33                 709           RLC     A
0237 F9                 710           MOV     R1,A
0238 E8                 711           MOV     A,R0
0239 33                 712           RLC     A
023A F8                 713           MOV     R0,A
                        714   ;
023B DCE6               715           DJNZ    R4,S2           ;DEC BIT COUNT
                        716   ;
023D EF                 717           MOV     A,R7            ;ROUND TO 8 BITS
023E 2401               718           ADD     A,#1
0240 FF                 719           MOV     R7,A
0241 EE                 720           MOV     A,R6
0242 3400               721           ADDC    A,#0
```

```
0244 13          722             RRC     A
0245 EF          723             MOV     A,R7
0246 13          724             RRC     A
                 725     ;
0247 22          726             RET
                 727     ;
                 728     ;##############################################################
                 729     ;
                 730     ; COMPUTE THE NORMALIZATION OFFSET.
                 731     ;
                 732     ; BIAS = TL - CL/M_UPPER
                 733     ;
                 734             PUBLIC  OFFSET
                 735             RSEG    ?GHT_2?PR
                 736     ;
                 737     OFFSET:
0248 7800        738             MOV     R0,#0           ;LOAD DIVIDEND (CL)
024A A900    F   739             MOV     R1,RESULT
024C AA00    F   740             MOV     R2,RESULT+1
024E 7D12        741             MOV     R5,#18          ;SET QUOTIENT BIT COUNT
0250 7E00        742             MOV     R6,#0           ;CLEAR QUOTIENT
0252 7F00        743             MOV     R7,#0
                 744     ;
0254 C3          745     02:     CLR     C               ;DIFFERENCE = DIVIDEND - DIVISOR
0255 E9          746             MOV     A,R1
0256 9500    F   747             SUBB    A,M_UPPER
0258 FB          748             MOV     R3,A
0259 E8          749             MOV     A,R0
025A 9400        750             SUBB    A,#0
                 751     ;
025C 4003        752             JC      01              ;JUMP IF UNDERFLOW
                 753     ;
025E F8          754             MOV     R0,A            ;DIVIDEND = DIFFERENCE
025F EB          755             MOV     A,R3
0260 F9          756             MOV     R1,A
                 757     ;
0261 B3          758     01:     CPL     C               ;SHIFT BIT INTO QUOTIENT
0262 EF          759             MOV     A,R7
0263 33          760             RLC     A
0264 FF          761             MOV     R7,A
0265 EE          762             MOV     A,R6
0266 33          763             RLC     A
0267 FE          764             MOV     R6,A
                 765     ;
0268 EA          766             MOV     A,R2            ;SHIFT DIVIDEND LEFT
0269 33          767             RLC     A
026A FA          768             MOV     R2,A
026B E9          769             MOV     A,R1
026C 33          770             RLC     A
026D F9          771             MOV     R1,A
026E E8          772             MOV     A,R0
026F 33          773             RLC     A
0270 F8          774             MOV     R0,A
                 775     ;
0271 DDE1        776             DJNZ    R5,02           ;DEC BIT COUNT
                 777     ;
                 778     ; ROUND TO UNITS
                 779     ;
```

```
0273 EF              780              MOV    A,R7
0274 2402            781              ADD    A,#2
0276 FF              782              MOV    R7,A
0277 EE              783              MOV    A,R6
0278 3400            784              ADDC   A,#0
027A 13              785              RRC    A
027B FE              786              MOV    R6,A
027C EF              787              MOV    A,R7
027D 13              788              RRC    A
027E FF              789              MOV    R7,A
027F C3              790              CLR    C
0280 EE              791              MOV    A,R6
0281 13              792              RRC    A
0282 FE              793              MOV    R6,A
0283 EF              794              MOV    A,R7
0284 13              795              RRC    A
0285 FF              796              MOV    R7,A
                     797         ;
0286 C3              798              CLR    C                    ;TL - QUOTIENT
0287 E500    F       799              MOV    A,SCRATCH+1
0289 9F              800              SUBB   A,R7
                     801         ;
028A 22              802              RET
                     803         ;
                     804         ;###############################################################
                     805         ;
                     806              END
```

SYMBOL TABLE LISTING

NAME          TYPE    VALUE       ATTRIBUTES

| NAME | TYPE | VALUE | | ATTRIBUTES |
|---|---|---|---|---|
| ?GMT_2?BI . | B SEG | 0001H | | REL=UNIT |
| ?GMT_2?DA . | D SEG | 0005H | | REL=UNIT |
| ?GMT_2?PR . | C SEG | 028BH | | REL=UNIT |
| ?READ?BYTE. | D ADDR | 0000H | R PUB | SEG=?GMT_2?DA |
| ?WRITE?BIT. | B ADDR | 0000H.0 | R PUB | SEG=?GMT_2?BI |
| ?WRITE?BYTE | D ADDR | 0003H | R PUB | SEG=?GMT_2?DA |
| ACC . . . . | D ADDR | 00E0H | A | |
| ACK . . . . | B ADDR | ---- | EXT | |
| B_1 . . . . | C ADDR | 0109H | R | SEG=?GMT_2?PR |
| B_2 . . . . | C ADDR | 00F1H | R | SEG=?GMT_2?PR |
| B . . . . . | D ADDR | 00F0H | A | |
| BIAS. . . . | D ADDR | ---- | EXT | |
| BLANK . . . | B ADDR | ---- | EXT | |
| BP. . . . . | NUMB | 0083H | A | |
| BUSY. . . . | C ADDR | 00EFH | R | SEG=?GMT_2?PR |
| CD_NORMAL . | C ADDR | 0179H | R PUB | SEG=?GMT_2?PR |
| CD_RATIO. . | C ADDR | 0125H | R PUB | SEG=?GMT_2?PR |
| CDN1. . . . | C ADDR | 0192H | R | SEG=?GMT_2?PR |
| CDN2. . . . | C ADDR | 0185H | R | SEG=?GMT_2?PR |
| CDN3. . . . | C ADDR | 01C4H | R | SEG=?GMT_2?PR |
| CDN4. . . . | C ADDR | 01CDH | R | SEG=?GMT_2?PR |
| CDN5. . . . | C ADDR | 0214H | R | SEG=?GMT_2?PR |
| CDN6. . . . | C ADDR | 01EFH | R | SEG=?GMT_2?PR |
| CDN7. . . . | C ADDR | 01E2H | R | SEG=?GMT_2?PR |
| CIR1. . . . | C ADDR | 013EH | R | SEG=?GMT_2?PR |

| | | | | | |
|---|---|---|---|---|---|
| CDR2. . . . . | C ADDR | 0133H | R | | SEG=?GMT_2?PR |
| CDR3. . . . . | C ADDR | 0156H | R | | SEG=?GMT_2?PR |
| COUNT . . . | D ADDR | 0002H | R | | SEG=?GMT_2?DA |
| DISPLAY . . | D ADDR | —— | | EXT | |
| EP. . . . . | NUMB | 0040H | A | | |
| F0. . . . . | B ADDR | 00D0H.5 | A | | |
| FAIL. . . . | B ADDR | —— | | EXT | |
| GMT_2 . . . | —— | —— | | | |
| LCD_1 . . . | C ADDR | 0013H | R | | SEG=?GMT_2?PR |
| LCD_2 . . . | C ADDR | 0006H | R | | SEG=?GMT_2?PR |
| LCD_3 . . . | C ADDR | 0039H | R | | SEG=?GMT_2?PR |
| LCD_4 . . . | C ADDR | 002BH | R | | SEG=?GMT_2?PR |
| LCD_DRIVE . | C ADDR | 0000H | R | PUB | SEG=?GMT_2?PR |
| M_LOWER . . | D ADDR | —— | | EXT | |
| M_UPPER . . | D ADDR | —— | | EXT | |
| MASK_0. . . | NUMB | 0048H | A | | |
| MASK_1. . . | NUMB | 00FFH | A | | |
| MASK_2. . . | NUMB | 00FFH | A | | |
| MASK_3. . . | NUMB | 00DAH | A | | |
| O1. . . . . | C ADDR | 0261H | R | | SEG=?GMT_2?PR |
| O2. . . . . | C ADDR | 0254H | R | | SEG=?GMT_2?PR |
| OFFSET. . . | C ADDR | 0248H | R | PUB | SEG=?GMT_2?PR |
| OUT_1 . . . | C ADDR | 010CH | R | | SEG=?GMT_2?PR |
| OUT . . . . | C ADDR | 010AH | R | | SEG=?GMT_2?PR |
| P0. . . . . | D ADDR | 0080H | A | | |
| P1. . . . . | D ADDR | 0090H | A | | |
| P2. . . . . | D ADDR | 00A0H | A | | |
| P3. . . . . | D ADDR | 00B0H | A | | |
| PAGE_WR . . | B ADDR | 0000H.0 | R | | SEG=?GMT_2?BI |
| POINT . . . | B ADDR | —— | | EXT | |
| R_1 . . . . | C ADDR | 0097H | R | | SEG=?GMT_2?PR |
| R_2 . . . . | C ADDR | 0086H | R | | SEG=?GMT_2?PR |
| R_3 . . . . | C ADDR | 0075H | R | | SEG=?GMT_2?PR |
| R_4 . . . . | C ADDR | 0098H | R | | SEG=?GMT_2?PR |
| R_5 . . . . | C ADDR | 003CH | R | | SEG=?GMT_2?PR |
| R_6 . . . . | C ADDR | 0073H | R | | SEG=?GMT_2?PR |
| RD_DST. . . | D ADDR | 0001H | R | | SEG=?GMT_2?DA |
| RD_SRC. . . | D ADDR | 0000H | R | | SEG=?GMT_2?DA |
| READ. . . . | C ADDR | 003AH | R | PUB | SEG=?GMT_2?PR |
| RESULT. . . | D ADDR | —— | | EXT | |
| S1. . . . . | C ADDR | 022EH | R | | SEG=?GMT_2?PR |
| S2. . . . . | C ADDR | 0223H | R | | SEG=?GMT_2?PR |
| SCL . . . . | NUMB | 0086H | A | | |
| SCRATCH . . | D ADDR | —— | | EXT | |
| SDA . . . . | NUMB | 0084H | A | | |
| SLOPE . . . | C ADDR | 0215H | R | PUB | SEG=?GMT_2?PR |
| TH1 . . . . | D ADDR | 008DH | A | | |
| TL. . . . . | D ADDR | —— | | EXT | |
| TL1 . . . . | D ADDR | 008BH | A | | |
| UPDATE. . . | B ADDR | —— | | EXT | |
| W_1 . . . . | C ADDR | 00EEH | R | | SEG=?GMT_2?PR |
| W_2 . . . . | C ADDR | 00B5H | R | | SEG=?GMT_2?PR |
| W_3 . . . . | C ADDR | 00DCH | R | | SEG=?GMT_2?PR |
| W_4 . . . . | C ADDR | 00D1H | R | | SEG=?GMT_2?PR |
| W_5 . . . . | C ADDR | 00A6H | R | | SEG=?GMT_2?PR |
| WR_DST. . . | D ADDR | 0004H | R | | SEG=?GMT_2?DA |
| WR_SRC. . . | D ADDR | 0003H | R | | SEG=?GMT_2?DA |

```
WRITE ... C ADDR    00A4H    R PUB    SEG=?GMT_2?PR

REGISTER BANK(S) USED: 0

ASSEMBLY COMPLETE, NO ERRORS FOUND
```

While particular embodiments of the invention have been shown and describe din detail, it will be obvious to those skilled in the art that changes and modifications of the present invention, in its various aspects, may be made without departing from the invention in its broader aspects, some of which changes and modifications being matters of routine engineering or design, and others being apparent only after study. As such, the scope of the invention should not be limited by the particular embodiment and specific construction described herein but should be defined by the appended claims and equivalents thereof. Accordingly, the aim in the appended claims is to cover all such changes and modifications as fall within the true spirit and scope of the invention.

The invention is claimed as follows:

1. Test apparatus for determining a given property, by weight, of a material, said apparatus comprising: wall means forming a chamber for receiving a sample of material to be tested, said chamber having an open top portion through which the material may be introduced therein for testing; electrical circuit means operatively coupled with said chamber for producing an electrical measurement signal corresponding to the said given property to be determined; indicator means for providing an observable indication of the said property of material in accordance with the corresponding electrical measurement signals; initiating means responsive to the accumulation of a predetermined measurement weight of material in said chamber for initiating the operation of said circuit means; said indicating means further including warning means responsive to the weight of material in said chamber reaching a second, predetermined warning weight slightly less than said predetermined measurement weight for producing a warning signal; said indicator means being responsive to said warning signal for producing a warning indication for alerting the operator to introduce material into the chamber more slowly to thereby reduce the inertia of material entering the chamber as the measurement weight is approached, to facilitate accuracy of the determination of the said given property of material, by weight; further including a base, wherein said initiating means comprises resilient means for supporting said chamber relative to said base, and an electrical circuit element actuatable between first, second and third states, actuator means for actuating said electrical circuit element from said first state to said second and third states in response to predetermined amounts of movement of said chamber relative to said base; and further including torsion means coupled intermediate said base and said chamber for resisting rotational motion of said chamber relative to said base to thereby substantially confine the forces exerted upon said chamber during introduction of material therein substantially to a direction for acting against the biasing force of said resilient means.

2. Apparatus according to claim 1, wherein said electrical circuit element comprises a switch having a contactor, a normally open contact and a normally closed contact; said switch being mounted for movement of the contactor relative the two contacts thereof in response to movement of the chamber relative to the base; said resilient means normally biasing said chamber to a position in which said contactor engages the normally closed contact with a predetermined biasing force; said predetermined biasing force being such that said contactor will disengage said normally closed contact upon the weight of material in said chamber reaching said warning weight and said contactor will engage said normally open contact upon the weight of material in said chamber reaching said measurement weight.

3. Apparatus according to claim 1 and further including means for adjusting the values of said predetermined measurement and warning weights.

4. Apparatus according to claim 1 wherein said circuit means further includes temperature compensation circuit means for producing a temperature compensation signal for varying the observable indication of said property of material in accordance with the variation in the temperature of a sample of material from a predetermined reference temperature.

5. Apparatus according to claim 1 wherein said circuit means includes memory means for containing predetermined data and information including calibration data for determining the said given property of a plurality of different materials in accordance with said measurement signal, and further including infrared programming link means for permitting access to said memory means for varying the data and information contained therein.

6. Apparatus according to claim 5 wherein said circuit means further includes calibration means for adjusting a bias setting on said calibration data in said memory means.

7. Apparatus according to claim 1 wherein said circuit means further includes inertia compensation means responsive to the inertia of material being introduced into the chamber for producing an inertia compensation signal for varying the observable indication of said property of material in accordance with the variation in the inertia of material being introduced into the chamber from a predetermined reference value.

8. Apparatus according to claim 1 wherein said wall means comprises respective inner and outer tubular wall members and a bottom wall member providing a closure for a bottom end of said chamber, said walls thereby defining an open-topped chamber therebetween of generally annular configuration, and wherein said resilient means comprises spring means, an elongate support member extending from said base and interiorly of the inner tubular wall member and spring mounting means for mounting said spring means intermediate said support member and said inner tubular wall member.

9. Apparatus according to claim 8 wherein said torsion means comprises at least one spiral flexure coupled intermediate said elongate support member and said inner wall member.

10. Test apparatus for determining a given property, by weight, of a material, said apparatus comprising: a test chamber for receiving a sample of material to be tested, said chamber having an open top portion through which the material may be introduced therein for testing; and electrical circuit means operatively coupled with said chamber for producing an electrical measurement signal corresponding to the said given property to be determined; wherein said circuit means includes memory means for containing predetermined data and information for determining the said property of a plurality of different materials in accordance with said measurement signal, and wherein said circuit means further includes inertia compensation means responsive to the inertia of material being introduced into the chamber and to a predetermined reference value for producing an inertia compensation signal and means for applying said inertia compensation signal to said measurement signal for compensating for errors in the measurement signal due to the variation in the inertia of material being introduced into the chamber from said predetermined reference value.

11. Apparatus according to claim 10 wherein said circuit means further includes temperature compensation circuit means for producing a temperature compensation signal for compensating for errors in said measurement signal due to variation in the temperature of a sample of material from a predetermined reference temperature.

12. Test apparatus for determining a given property, by weight, of a material, said apparatus comprising: wall means forming a chamber for receiving a sample of material to be tested, said chamber having an open top portion through which the material may be introduced therein for testing; electrical circuit means operatively coupled with said chamber for producing an electrical measurement signal corresponding to the said given property to be determined; indicator means for providing an observable indication of the said property of material in accordance with the corresponding electrical measurement signals; initiating means responsive to the accumulation of a predetermined measurement weight of material in said chamber for initiating the operation of said circuit means; said indicating means further including warning means responsive to the weight of material in said chamber reaching a second, predetermined warning weight slightly less than said predetermined measurement weight for producing a warning signal; said indicator means being responsive to said warning signal for producing a warning indication for alerting the operator to introduce material into the chamber more slowly to thereby reduce the inertia of material entering the chamber as the measurement weight is approached, to facilitate accuracy of the determination of the said given property of material, by weight; further including a base, wherein said initiating means comprises resilient means for supporting said chamber relative to said base, and an electrical circuit element actuatable between first, second and third states, actuator means for actuating said electrical circuit element from said first state to said second and third states in response to predetermined amounts of movement of said chamber relative to said base; wherein said electrical circuit element comprises a switch having a contactor, a normally open contact and a normally closed contact; said switch being mounted for movement of the contactor relative the two contacts thereof in response to movement of the chamber relative to said base, said resilient means normally biasing said chamber to a position in which said contactor engages the normally closed contact with a predetermined biasing force; said predetermined biasing force being such that said contactor will disengage said normally closed contact upon the weight of material in said chamber reaching said warning weight and said contactor will engage said normally open contact upon the weight of material in said chamber reaching said measurement weight.

13. Test apparatus for determining a given property, by weight, of a material, said apparatus comprising: wall means forming a chamber for receiving a sample of material to be tested, said chamber having an open top portion through which the material may be introduced therein for testing; electrical circuit means operatively coupled with said chamber for producing an electrical measurement signal corresponding to the said given property to be determined; indicator means for providing an observable indication of the said property of material in accordance with the corresponding electrical measurement signals; initiating means responsive to the accumulation of a predetermined measurement weight of material in said chamber for initiating the operation of said circuit means; said indicating means further including warning means responsive to the weight of material in said chamber reaching a second, predetermined warning weight slightly less than said predetermined measurement weight for producing a warning signal; said indicator means being responsive to said warning signal for producing a warning indication for alerting the operator to introduce material into the chamber more slowly to thereby reduce the inertia of material entering the chamber as the measurement weight is approached, to facilitate accuracy of the determination of the said given property of material, by weight; further including a base, wherein said initiating means comprises resilient means for supporting said chamber relative to said base, and an electrical circuit element actuatable between first, second and third states, actuator means for actuating said electrical circuit element from said first state to said second and third states in response to predetermined amounts of movement of said chamber relative to said base; wherein said wall means comprises respective inner and outer tubular wall members and a bottom wall member providing a closure for a bottom end of said chamber, said walls thereby defining an open-topped chamber therebetween of generally annular configuration, and wherein said resilient means comprises spring means, an elongate support member extending from said base and interiorly of the inner tubular wall member and spring mounting means for mounting said spring means intermediate said support member and said inner tubular wall member.

* * * * *